US009889194B2

(12) United States Patent
Jiang et al.

(10) Patent No.: US 9,889,194 B2
(45) Date of Patent: Feb. 13, 2018

(54) IMMUNOGENIC COMPOSITION FOR MERS CORONAVIRUS INFECTION

(71) Applicants: New York Blood Center, Inc., New York, NY (US); Yusen Zhou, Beijing (CN); Guangyu Zhao, Beijing (CN)

(72) Inventors: Shibo Jiang, New York, NY (US); Lanying Du, New York, NY (US); Yusen Zhou, Beijing (CN); Guangyu Zhao, Beijing (CN)

(73) Assignee: New York Blood Center, Inc., New York, NY (US)

( * ) Notice: Subject to any disclaimer, the term of this patent is extended or adjusted under 35 U.S.C. 154(b) by 429 days.

(21) Appl. No.: 14/375,083

(22) PCT Filed: Feb. 28, 2014

(86) PCT No.: PCT/US2014/019402
§ 371 (c)(1),
(2) Date: Jul. 28, 2014

(87) PCT Pub. No.: WO2014/134439
PCT Pub. Date: Sep. 4, 2014

(65) Prior Publication Data
US 2016/0296617 A1   Oct. 13, 2016

Related U.S. Application Data

(60) Provisional application No. 61/771,561, filed on Mar. 1, 2013, provisional application No. 61/941,076, filed on Feb. 18, 2014.

(51) Int. Cl.
| | |
|---|---|
| *A61K 39/215* | (2006.01) |
| *C07K 16/10* | (2006.01) |
| *C12N 7/00* | (2006.01) |
| *A61K 39/12* | (2006.01) |
| *C07K 14/005* | (2006.01) |
| *A61K 39/385* | (2006.01) |
| *A61K 39/00* | (2006.01) |

(52) U.S. Cl.
CPC ........... *A61K 39/215* (2013.01); *A61K 39/12* (2013.01); *C07K 14/005* (2013.01); *C07K 16/10* (2013.01); *C12N 7/00* (2013.01); *A61K 2039/55561* (2013.01); *A61K 2039/55566* (2013.01); *A61K 2039/575* (2013.01); *C07K 2319/21* (2013.01); *C07K 2319/30* (2013.01); *C12N 2770/20021* (2013.01); *C12N 2770/20022* (2013.01); *C12N 2770/20034* (2013.01)

(58) Field of Classification Search
CPC .................. C07K 16/10; A61K 39/215; A61K 2039/55561; A61K 2039/55566; A61K 38/00; G01N 2333/165
See application file for complete search history.

(56) References Cited

U.S. PATENT DOCUMENTS

| | | |
|---|---|---|
| 8,936,789 B2 | 1/2015 | Jiang et al. |
| 2006/0257852 A1 | 11/2006 | Rappuoli et al. |
| 2011/0086058 A1 | 4/2011 | Jiang et al. |
| 2015/0017207 A1 | 1/2015 | Gale et al. |

FOREIGN PATENT DOCUMENTS

| | | |
|---|---|---|
| CN | 103554235 A | 2/2014 |
| WO | 2005-018538 A2 | 3/2005 |
| WO | 2014121132 | 8/2014 |
| WO | 2014045254 | 2/2015 |
| WO | 2015042373 | 3/2015 |
| WO | 2015057942 | 4/2015 |
| WO | 2015057966 | 4/2015 |
| WO | 2015081155 | 6/2015 |

OTHER PUBLICATIONS

Qiu et al. Microbiology and immunology, 2012, vol. 56, pp. 554-561.*
Chen et al. Journal of Virology, 2013, vol. 87, No. 19, pp. 10777-10783.*
Edmund et al. Arch. Immunol. Ther. Exp. 2009, vol. 57, pp. 311-323.*
Du et al., "A truncated receptor-binding domain of MERS-CoV spike protein potently inhibits MERS-CoV infection and induces strong neutralizing antibody responses: implication for developing therapeutics and vaccines", Plos One, vol. 8, No. 12, Article No. e81587, pp. 1-9, Dec. 2013.
He et al., "Identification of immunodominant sites on the spike protein of severe acute respiratory syndrome (SARS) coronavirus: implication for developing SARS diagnostics and vaccines", The Journal of Immunology, vol. 173, No. 6, pp. 4050-4057, Sep. 15, 2004.
Zaki et al., "Isolation of a novel coronavirus from a man with pneumonia in Saudi Arabia", The new England Journal of Medicine, vol. 367, No. 19, pp. 1814-1820, Nov. 8, 2012.
Perlman S. "The Middle East Respiratory Syndrome—How worried should we be?" mBio 4:e00531-13, 2013.
Perlman et al. "Human coronavirus EMC is not the same as Severe Acute Respiratory Syndrome coronavirus," mBio 4:e00002-13, 2013.
Van Boheemen et al. "Genomic characterization of a newly discovered coronavirus associated with Acute Respiratory Distress Syndrome in humans," mBio 3:e00473-12, 2012.
Jiang et al., A predicated receptor-binding and critical neutralizing domain in S protein of the novel human coronavirus HCoV-EMC. Journal of Infection, Letters to the Editor, vol. 66, No. 5, pp. 464-466 (2012).

(Continued)

*Primary Examiner* — Bao Li
(74) *Attorney, Agent, or Firm* — K&L Gates LLP; Louis C. Cullman; Michelle Glasky Bergman

(57) ABSTRACT

Described herein are immunogenic compositions for preventing infection with Middle East respiratory syndrome coronavirus (MERS-CoV) wherein the immunogenic compositions comprise at least a portion of the MERS-CoV S protein and an immunopotentiator.

23 Claims, 18 Drawing Sheets

(56) References Cited

OTHER PUBLICATIONS

Du et al., The spike protein of SARS-CoV—a target for vaccine and therapeutic development. Nature Reviews, Microbiology, vol. 7, No. 3, pp. 226-236 (2009).

Yan et al., Strategies for designing peptide immunogens to elicit [alpha]-helical conformation-specific antibodies reactive with native proteins. ACS Symposium Series, vol. 1095, pp. 93-136 (2012).

Du et al., Identification of a receptor-binding domain in the S protein of the novel human coronavirus middle east respiratory syndrome coronavirus as an essential target for vaccine development. Journal of Virology, vol. 87, No. 17, pp. 9939-9942 (2013).

Gierer et al., The spike protein of the emerging betacoronavirus EMC uses a novel coronavirus receptor for entry, can be activated by TMPRSS2, and is targeted by neutralizing antibodies. Journal of Virology, vol. 87, No. 10, pp. 5502-5511 (2013).

Wang et al., Structure of MERS-CoV spike receptor-binding domain complexed with human receptor DPP4. Cell Research, 23:986-993 (2013).

Raj et al., Dipeptidyl peptidase 4 is a functional receptor for the emerging human coronavirus—EMC. Nature, vol. 495, pp. 251-256 (2013).

Lu et al., Molecular basis of binding between novel human coronavirus MERS-CoV and its receptor CD26. Nature, vol. 500, pp. 227-232 (2013).

Zhou et al., The receptor binding domain of MERS-CoV: the dawn of vaccine and treatment development. Journal of the Formosan Medical Association, 113:143-147 (2013).

Supplementary European Search Report dated Sep. 26, 2016 for European Patent Application No. EP 14757347.1 filed on Feb. 28, 2014.

* cited by examiner

IMMUNOGENIC COMPOSITION FOR MERS CORONAVIRUS INFECTION

CROSS REFERENCE TO RELATED APPLICATIONS

The present application is an application under section 371 of International patent application PCT/US2014/019402 filed Feb. 28, 2014, which claims the benefit under 35 U.S.C. 119(e) to U.S. Provisional patent applications 61/771,561 filed Mar. 1, 2013 and 61/941,076 filed Feb. 18, 2014, the entire contents of all of which are incorporated by reference herein.

GOVERNMENT SUPPORT STATEMENT

This invention was made with government support under Grant Number AI109094 awarded by the National Institutes of Health. The Government has certain rights in the invention.

FIELD OF THE INVENTION

The present disclosure relates to the field of immunogenic compositions for the prevention and treatment of infection with human MERS coronavirus.

BACKGROUND

Coronaviruses infect and cause disease in a wide variety of species, including bats, birds, cats, dogs, pigs, mice, horses, whales, and humans. Bats act as a natural reservoir for coronaviruses. Most infections caused by human coronaviruses are relatively mild. However, the outbreak of severe acute respiratory syndrome (SARS) caused by SARC-CoV in 2002-2003, and fatal infection in 2012 caused by a recently identified coronavirus, Middle East respiratory syndrome coronavirus (MERS-CoV, also known as hCoV-EMC or NCoV) demonstrated that coronaviruses are also able to cause severe, sometimes fatal disease in humans.

The recently identified coronavirus MERS-CoV has over 40% mortality rate among the infected individuals. This virus also demonstrates person-to-person transmission, posing a continuous threat to public health worldwide. Thus, development of vaccines and antiviral agents against this new virus are urgently needed.

SUMMARY

Disclosed herein are immunogenic compositions for the prevention or treatment of infection with a new coronavirus MERS-CoV (also known as hCoV-EMC or NCoV). The disclosed immunogenic compositions are proteins comprising: 1) at least a portion of the MERS-CoV genome, and 2) an immunopotentiator sequence. The sequences are contiguous and expressed as a single protein in a mammalian expression system, or the MERS-CoV portion and the immunopotentiator are chemically linked and stabilized. Optionally, a stabilization sequence and/or a linker sequence are disposed between the MERS-CoV sequence and the immunopotentiator.

Thus, provided herein is a protein comprising a Middle East respiratory syndrome coronavirus (MERS-CoV) spike (S) protein sequence, or fragment thereof; and an immunopotentiator. In one embodiment, the MERS-CoV S protein sequence comprises an MERS-CoV S1 protein sequence, or a fragment thereof; a receptor-binding domain (RBD) sequence of an MERS-CoV S protein, or a fragment thereof; a fusion peptide sequence of an MERS-CoV S protein, or a fragment thereof; a heptad repeat sequence of an MERS-CoV S protein, or a fragment thereof; a nucleocapsid sequence of an MERS-CoV S protein, or a fragment thereof; or a membrane sequence of an MERS-CoV S protein, or a fragment thereof. In another embodiment, the MERS-CoV S protein sequence comprises amino acids 377-588 of the MERS-CoV S protein sequence (SEQ ID NO:3).

Also disclosed herein are immunogenic compositions comprising a protein, the protein comprising a MERS-CoV S protein sequence, or fragment thereof; and an immunopotentiator. In one embodiment, the MERS-CoV S protein sequence comprises an MERS-CoV S1 protein sequence, or a fragment thereof; a receptor-binding domain (RBD) sequence of an MERS-CoV S protein, or a fragment thereof; a fusion peptide sequence of an MERS-CoV S protein, or a fragment thereof; a heptad repeat sequence of an MERS-CoV S protein, or a fragment thereof; a nucleocapsid sequence of an MERS-CoV S protein, or a fragment thereof; or a membrane sequence of an MERS-CoV S protein, or a fragment thereof. In another embodiment, the MERS-CoV S protein sequence comprises amino acids 377-588 of the MERS-CoV S protein sequence (SEQ ID NO:3).

In another embodiment, the MERS-CoV S protein sequence is 85% identical to the MERS-CoV S protein sequence, the MERS-CoV S1 protein sequence, the RBD sequence of the MERS-CoV S protein, the fusion peptide sequence of the MERS-CoV S protein, the heptad repeat sequence of the MERS-CoV S protein, the nucleocapsid sequence of the MERS-CoV S protein, or the membrane sequence of the MERS-CoV S protein, or a fragment thereof.

In another embodiment, the MERS-CoV S protein sequence is 90% identical to the MERS-CoV S protein sequence, the MERS-CoV S1 protein sequence, the RBD sequence of the MERS-CoV S protein, the fusion peptide sequence of the MERS-CoV S protein, the heptad repeat sequence of the MERS-CoV S protein, the nucleocapsid sequence of the MERS-CoV S protein, or the membrane sequence of the MERS-CoV S protein, or a fragment thereof.

In yet another embodiment, the MERS-CoV S protein sequence is 95% identical to the MERS-CoV S protein sequence, the MERS-CoV S1 protein sequence, the RBD sequence of the MERS-CoV S protein, the fusion peptide sequence of the MERS-CoV S protein, the heptad repeat sequence of the MERS-CoV S protein, the nucleocapsid sequence of the MERS-CoV S protein, or the membrane sequence of the MERS-CoV S protein, or a fragment thereof.

In one embodiment, the immunopotentiator sequence is an Fc fragment of human IgG (Fc), a C3d protein, an *Onchocerca volvulus* ASP-1, a cholera toxin, a muramyl peptide, or a cytokine. In another embodiment, the immunopotentiator is Fc.

In another embodiment, the protein further comprises a stabilization sequence disposed between the MERS-CoV S protein sequence and the immunopotentiator sequence. In another embodiment, the stabilization sequence is a foldon (Fd) or GCN4.

In yet another embodiment, the protein further comprises a linker sequence disposed between the MERS-CoV S protein sequence and the immunopotentiator sequence, and the linker is $(GGGGS)_n$, wherein n is an integer between 0 and 8. In another embodiment, n is 1.

In another embodiment, the protein is produced in a mammalian expression system.

In another embodiment, the protein comprises the sequence of S377-588-Fc (SEQ ID NO:12).

In another embodiment, the immunogenic composition further comprises an adjuvant.

Also provided is a method of inducing a protective immune response against MERS-CoV comprising administering the immunogenic composition of claim 20 to a subject in need thereof; wherein the immunogenic composition induces a protective immune response against challenge with MERS-CoV in the host.

In another embodiment, the immunogenic composition further comprises an adjuvant.

In one embodiment, the administering step comprises a prime immunization and at least one boost immunization. In another embodiment, the boost immunizations are administered at least twice. In another embodiment, n the boost immunizations are administered weekly, every other week, monthly, or every other month. In yet another embodiment, the boost immunizations are administered weekly, every 2 weeks, every 3 weeks, every 4 weeks, every 5 weeks, every 6 weeks, every 7 weeks, every 8 weeks, every 9 weeks, every 10 weeks, every 11 weeks, or every 12 weeks.

BRIEF DESCRIPTION OF THE DRAWINGS

FIG. 4A and FIG. 4B depict the antibody responses and neutralization induced by MERS-CoV S377-662-Fc protein. FIG. 4A depicts binding to MERS-CoV S377-662 and SARS-CoV S-RBD proteins by antibodies in mouse sera collected 10 days post-$2^{nd}$ immunization. The data are presented as mean A450±SD of five mice per group at various dilution points. FIG. 4B depicts neutralization of the MERS-CoV virus by the same antisera as in FIG. 4A. Neutralizing antibody titers were expressed as the reciprocal of the highest dilution of sera that completely inhibited virus-induced cytopathic effect (CPE) in at least 50% of the wells ($NT_{50}$), and are presented as mean±SD from five mice per group.

FIG. 6A depicts binding of IgG to a MERS-CoV S1 protein containing residues 18-725 of MERS-CoV S1 with a His6 tag (S1-His). Sera from 10 days post-last immunization were used for the detection, and the data are presented as mean A450±SD of five mice per group at various dilution points. FIG. 6B depicts the long-term IgG antibody responses using sera collected at 0, 1, 2, 3, 4, 6 months after the first immunization and 10 days post-last immunization. The data are presented as mean (IgG endpoint titers)±SD of five mice per group.

FIG. 16A depicts S377-588-Fc protein (black line, right) bound to Huh-7 cells (gray shade), while the control human IgG Fc protein (black line, left) did not exhibit binding activity. FIG. 16B depicts the inhibition of S377-588-Fc binding to Huh-7 cells (gray shade) by sera from mice immunized with S377-588-Fc (white line), but not by sera from the PBS control group (black line).

DETAILED DESCRIPTION

Development of an effective and safe vaccine against a newly recognized coronavirus MERS-CoV (also known as hCoV-EMC or NCoV) is urgently needed for the prevention of current spread and future outbreaks. The present disclosure describes the development of a MERS-CoV immunogenic composition based on the spike (S) protein of MERS-CoV. This immunogenic composition induced strong immune responses and potent neutralizing antibodies in immunized animals.

As used herein the term "immunogen" refers to any substrate that elicits an immune response in a host. As used herein an "immunogenic composition" refers to an expressed protein or a recombinant vector, with or without an adjuvant, which expresses and/or secretes an immunogen in vivo and wherein the immunogen elicits an immune response in the host. The immunogenic compositions disclosed herein may or may not be immunoprotective or therapeutic. When the immunogenic compositions may prevent, ameliorate, palliate, or eliminate disease from the host then the immunogenic composition may also optionally be referred to as a vaccine. However, the term immunogenic composition is not intended to be limited to vaccines.

MERS-CoV is closely related to severe acute respiratory syndrome (SARS) coronavirus (SARS-CoV). Clinically similar to SARS, MERS-CoV infection leads to severe respiratory illness with renal failure. As the sixth coronavirus known to infect humans and the first human coronavirus in lineage C of betacoronavirus (the same lineage as Bat-CoV-HKU-4 and -HKU-5), MERS-CoV is closely related to SARS-CoV genetically (lineage B). Therefore, MERS-CoV has recently raised serious concerns of a potential pandemic and, as such, it poses a continuous threat to public health worldwide. Human dipeptidyl peptidase 4 (DPP4) has been identified as the MERS-CoV's receptor.

Like other coronaviruses, the MERS-CoV virion utilizes a large surface S glycoprotein for interaction with, and entry into, the target cell. The S glycoprotein consists of a globular S1 domain at the N-terminal region, followed by membrane-proximal S2 domain, a transmembrane domain, and an intracellular domain.

Figures 9A, 9B:
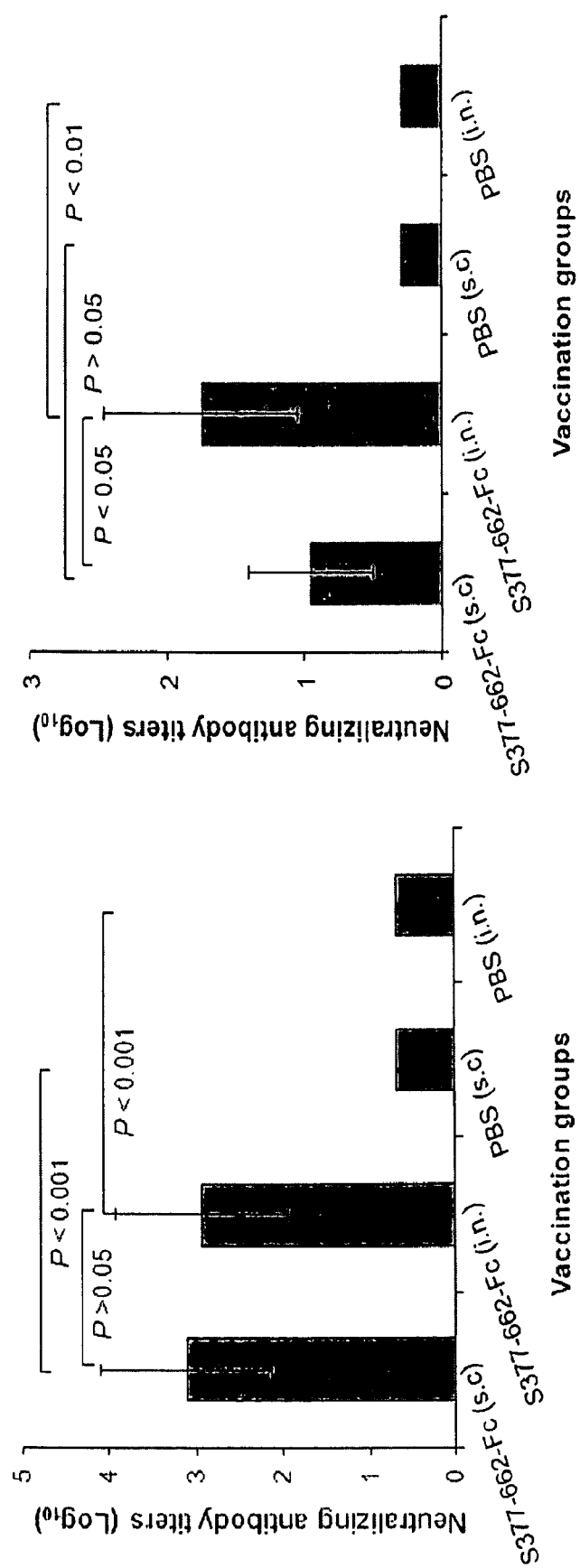
FIG. 9A and FIG. 9B depict the neutralizing antibody titer against MERS-CoV infection from samples of mice immunized (s.c. and i.n.) with MERS-CoV S377-662-Fc protein. Sera (FIG. 9A) and lung wash (1:1,000 dilution in PBS during collection) (FIG. 9B) were collected at 10 days post-last immunization and analyzed for neutralization of MERS-CoV infection in Vero E6 cells. Neutralizing antibody titers were expressed as the $NT_{50}$, and are presented as GMT±SD from five mice per group. P<0.05 indicates significant difference.
Figure 15:
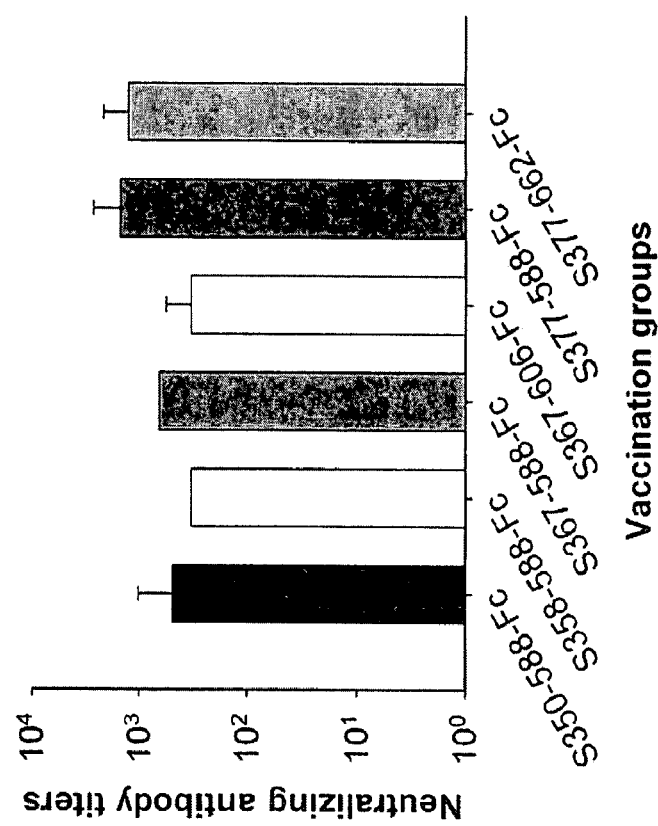
FIG. 15 depicts the neutralizing antibody titer of antisera from mice immunized s.c. with MERS-CoV RBD-Fc proteins against MERS-CoV infection in Vero E6 cells. Sera from 10 days post-3$^{rd}$ immunization were used for the assay. Neutralizing antibody titers were expressed as the $NT_{50}$, and are presented as mean±SD from five mice per group.
Figures 16A, 16B:
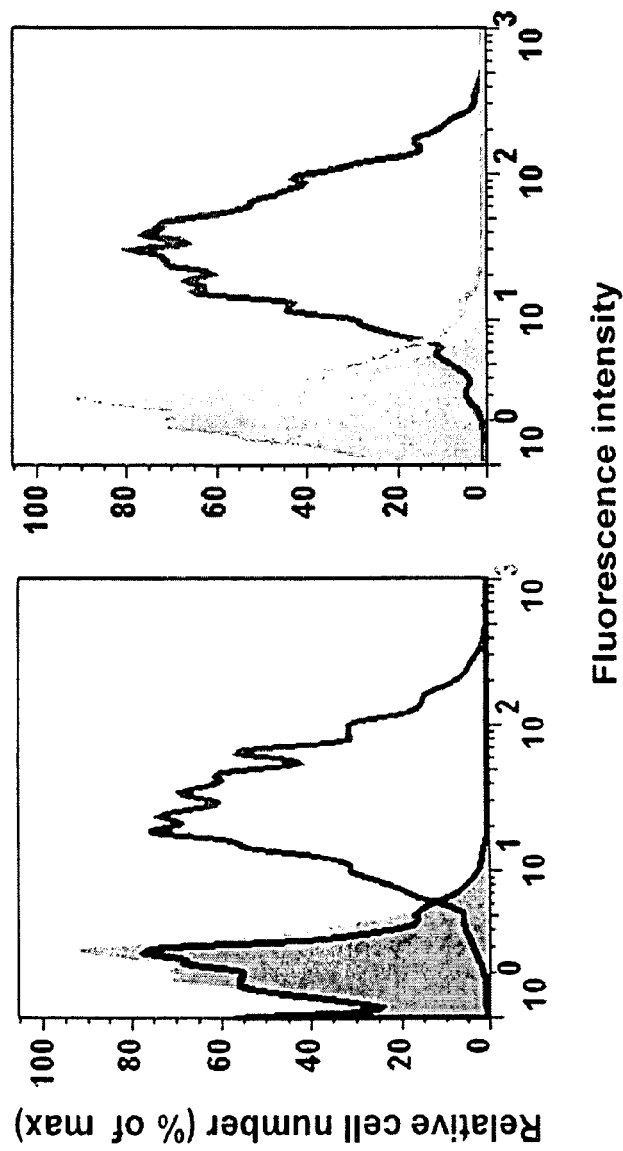
FIG. 16A and FIG. 16B depict the flow cytometry detection of inhibition of MERS-CoV RBD-Fc protein (S377-588-Fc) binding to Huh-7 cells expressing DPP4 receptor by antisera from mice immunized with S377-588-Fc protein.
Figure 17:
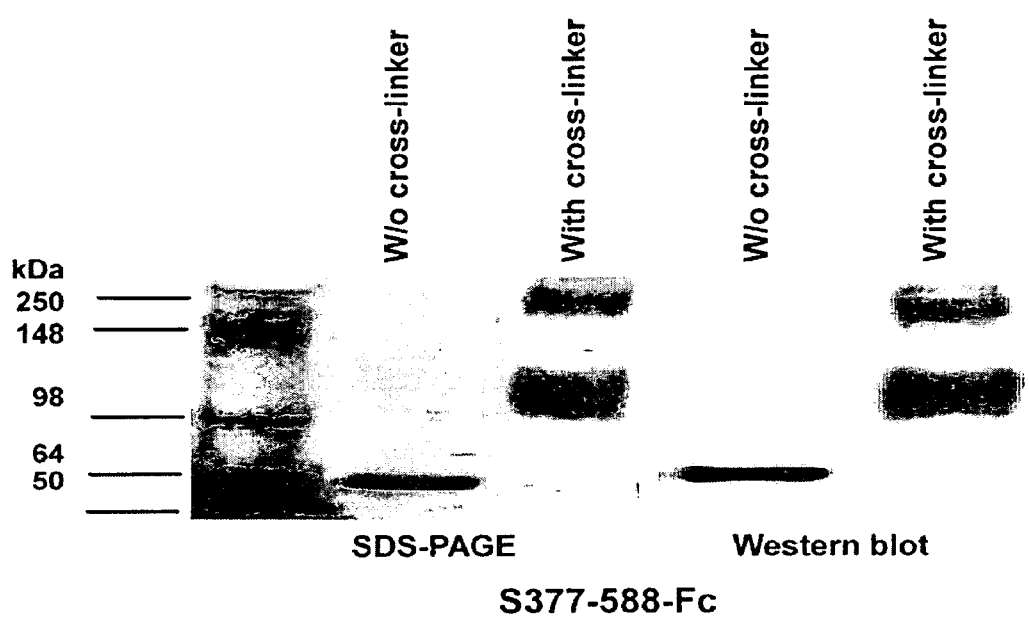
FIG. 17 depicts the conformational structure of MERS-CoV S377-588-Fc protein by cross-linker analysis. The protein was cross-linked with glutaraldehyde or left uncross-linked (w/o cross-linker), followed by Western blot detection using antisera (1:1,000) from mice immunized with MERS-CoV 51-His. The protein molecular weight marker (kDa) is indicated on the left.
Figure 18:
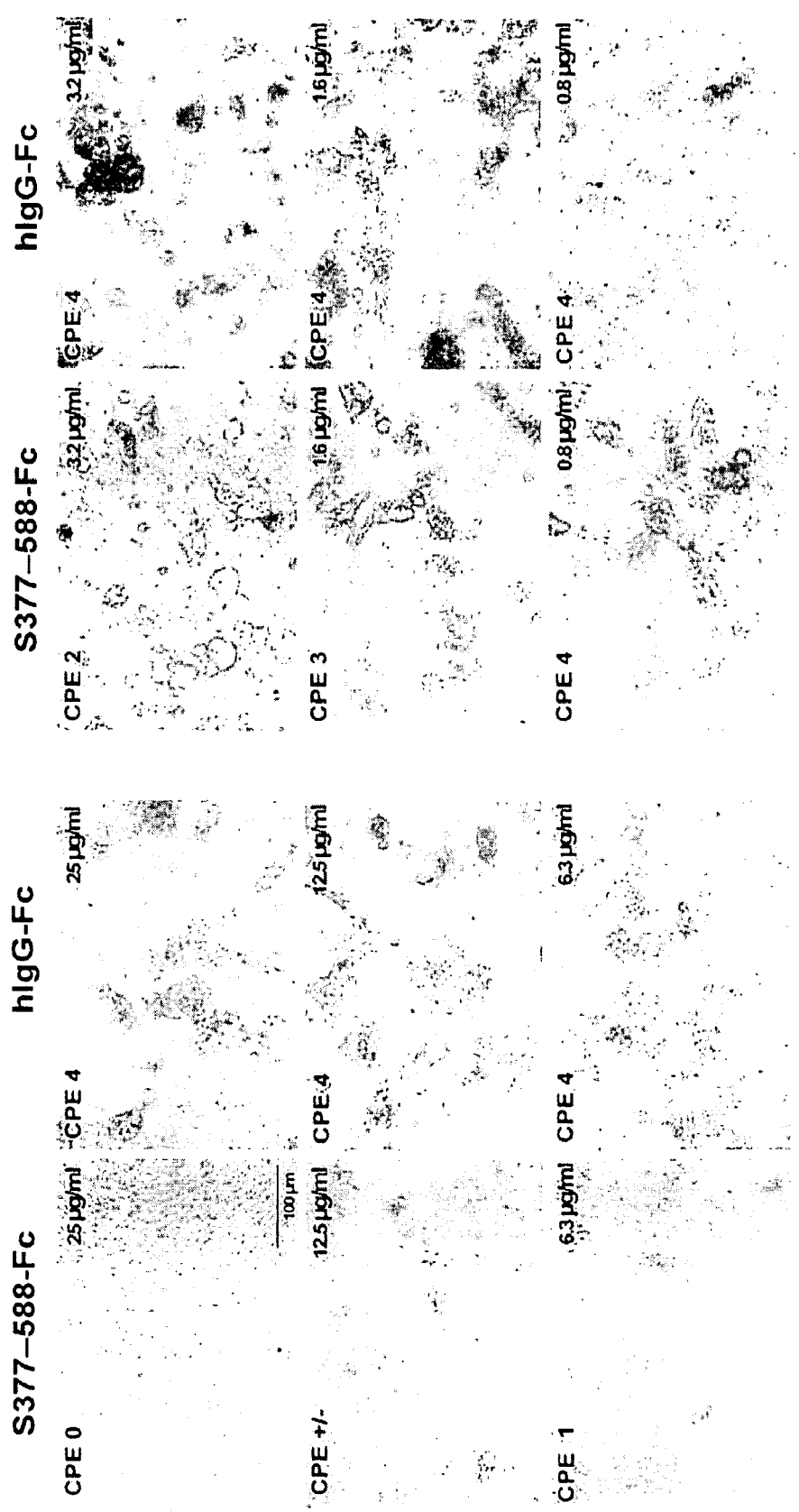
FIG. 18 depicts the inhibition of MERS-CoV infection in Calu-3 cells by MERS-CoV S377-588-Fc protein. Human IgG Fc (hIgG-Fc) was used as the control. The CPE ranged from 0 (none), ±(<5%), 1 (5-10%), 2 (10-25%), 3 (25-50%), and 4 (>50%).

The receptor-binding domain (RBD) of SARS-CoV S protein contains a critical neutralizing domain (CND), which induces potent neutralizing antibodies and protection against SARS-CoV infection in animal models. By comparing and analyzing the S protein sequences of MERS-CoV and SARS-CoV, it was found that the S1 subunit encompassing residues 377-662 of MERS-CoV S protein exhibited a core structure very similar to that of SARS-CoV S protein, suggesting that this region of MERS-CoV S protein also serves as a neutralizing domain. Indeed, a recombinant protein containing residues 377-662 of MERS-CoV S fused to Fc (fragment, crystallizable) domain of human IgG (S377-662-Fc, FIG. 1) was expressed in a mammalian cell expression system (FIG. 2) and is able to induce neutralizing antibodies through both subcutaneous (s.c.) and intranasal (i.n.) routes of administration in an established mouse model of MERS-CoV (FIG. 9). Additionally, recombinant RBD protein fragments spanning residues 350-606 of MERS-CoV S protein were fused to the Fc domain of human IgG (e.g., S350-588-Fc, S358-588-Fc, S367-588-Fc, S377-588-Fc, S367-606-Fc), were expressed in the mammalian cell expression system (FIG. 11), and elicited neutralizing antibodies in immunized mice (FIG. 15). Particularly, a truncated RBD region containing residues 377-588 of MERS-CoV S protein fused to Fc of human IgG (S377-588-Fc) induced a potent neutralizing antibody response in immunized mice (FIG. 15). Antisera from mice immunized with this protein effectively blocked the RBD protein binding to MERS-CoV's receptor DPP4 (FIG. 16). Furthermore, the S377-588-Fc protein was able to form dimeric or tetrameric conformational structures (FIG. 17), and effectively inhibited MERS-CoV infection in DPP4-expressing Calu-3 cells (FIG. 18).

In one embodiment, the S protein sequence component of the instant immunogenic composition comprises a MERS-CoV S protein sequence, a MERS-CoV S1 protein sequence, a MERS-CoV S2 protein sequence, an RBD sequence of a MERS-CoV S protein, a fusion sequence of a MERS-CoV S protein, a heptad repeat sequence of a MERS-CoV S protein, a nucleocapsid sequence of a MERS-CoV S protein, a membrane sequence of a MERS-CoV S protein, or a portion of any of these sequences. In one embodiment, the S protein sequence comprises amino acids 377-662 (SEQ ID NO:2), 377-588 (SEQ ID NO:3), 350-588 (SEQ ID NO:4), 358-588 (SEQ ID NO:5), 367-588 (SEQ ID NO:6), or 367-606 (SEQ ID NO:7) of MERS-CoV S protein.

TABLE 1

Amino acid sequences of MERS-CoV regions and immunopotentiators

SEQ ID NO. 1 [MERS-CoV S protein]:
MIHSVFLLMFLLTPTESYVDVGPDSVKSACIEVDIQQTFFDKTWPRPIDV
SKADGIIYPQGRTYSNITITYQGLFPYQGDHGDMYVYSAGHATGTTPQKL
FVANYSQDVKQFANGFVVRIGAAANSTGTVIISPSTSATIRKIYPAFMLG
SSVGNFSDGKMGRFFNHTLVLLPDGCGTLLRAFYCILEPRSGNHCPAGNS
YTSFATYHTPATDCSDGNYNRNASLNSFKEYFNLRNCTFMYTYNITEDEI
LEWFGITQTAQGVHLFSSRYVDLYGGNMFQFATLPVYDTIKYYSIIPHSI
RSIQSDRKAWAAFYVKLQPLTFLLDFSVDGYIRRAIDCGFNDLSQLHCS
YESFDVESGVYSVSSFEAKPSGSVVEQAEGVECDFSPLLSGTPPQVYNFK
RLVFTNCNYNLTKLLSLFSVNDFTCSQISPAAIASNCYSSLILDYFSYPL
SMKSDLSVSSAGPISQFNYKQSFSNPTCLILATVPHNLTTITKPLKYSYI
NKCSRLLSDDRTEVPQLVNANQYSPCVSIVPSTVWEDGDYYRKQLSPLEG
GGWLVASGSTVAMTEQLQMGFGITVQYGTDTNSVCPKLEFANDTKIASQL
GNCVEYSLYGVSGRGVFQNCTAVGVRQQRFVYDAYQNLVGYYSDDGNYYC
LRACVSVPVSVIYDKETKTHATLFGSVACEHISSTMSQYSRSTRSMLKRR
DSTYGPLQTPVGCVLGLVNSSLFVEDCKLPLGQSLCALPDTPSTLTPRSV
RSVPGEMRLASIAFNHPIQVDQLNSSYFKLSIPTNFSFGVTQEYIQTTIQ
KVTVDCKQYVCNGFQKCEQLLREYGQFCSKINQALHGANLRQDDSVRNLF
ASVKSSQSSPIIPGFGGDFNLTLLEPVSISTGSRSARSAIEDLLFDKVTI
ADPGYMQGYDDCMQQGPASARDLICAQYVAGYKVLPPLMDVNMEAAYTSS
LLGSIAGVGWTAGLSSFAAIPFAQSIFYRLNGVGITQQVLSENQKLIANK
FNQALGAMQTGFTTTNEAFQKVQDAVNNNAQALSKLASELSNTFGAISAS
IGDIIQRLDVLEQDAQIDRLINGRLTTLNAFVAQQLVRSESAALSAQLAK
DKVNECVKAQSKRSGFCGQGTHIVSFVVNAPNGLYFMHVGYYPSNHIEVV
SAYGLCDAANPTNCIAPVNGYFIKTNNTRIVDEWSYTGSSFYAPEPITSL
NTKYVAPQVTYQNISTNLPPPLLGNSTGIDFQDELDEFFKNVSTSINPFG
SLTQINTTLLDLTYEMLSLQQVVKALNESYIDLKELGNYTYYNKWPWYIW
LGFIAGLVALALCVFFILCCTGCGTNCMGKLKCNRCCDRYEEYDLEPHKV
HVH SEQ ID NO. 2 [aa377-662 of MERS-CoV S protein]:
QAEGVECDFSPLLSGTPPQVYNFKRLVFTNCNYNLTKLLSLFSVNDFTCS
QISPAAIASNCYSSLILDYFSYPLSMKSDLSVSSAGPISQFNYKQSFSNP
TCLILATVPHNLTTITKPLKYSYINKCSRLLSDDRTEVPQLVNANQYSPC
VSIVPSTVWEDGDYYRKQLSPLEGGGWLVASGSTVAMTEQLQMGFGITVQ
YGTDTNSVCPKLEFANDTKIASQLGNCVEYSLYGVSGRGVFQNCTAVGVR
QQRFVYDAYQNLVGYYSDDGNYYCLRACVSVPVSVI SEQ ID NO. 3 [aa377-588 of MERS-CoV S protein]:
QAEGVECDFSPLLSGTPPQVYNFKRLVFTNCNYNLTKLLSLFSVNDFTCS
QISPAAIASNCYSSLILDYFSYPLSMKSDLSVSSAGPISQFNYKQSFSNP
TCLILATVPHNLTTITKPLKYSYINKCSRLLSDDRTEVPQLVNANQYSPC
VSIVPSTVWEDGDYYRKQLSPLEGGGWLVASGSTVAMTEQLQMGFGITVQ
YGTDTNSVCPKL SEQ ID NO. 4 [aa350-588 of MERS-CoV S protein]:
SYESFDVESGVYSVSSFEAKPSGSVVEQAEGVECDFSPLLSGTPPQVYNF
KRLVFTNCNYNLTKLLSLFSVNDFTCSQISPAAIASNCYSSLILDYFSYP
LSMKSDLSVSSAGPISQFNYKQSFSNPTCLILATVPHNLTTITKPLKYSY
INKCSRLLSDDRTEVPQLVNANQYSPCVSIVPSTVWEDGDYYRKQLSPLE
GGGWLVASGSTVAMTEQLQMGFGITVQYGTDTNSVCPKL SEQ ID NO. 5 [aa358-588 of MERS-CoV S protein]:
SGVYSVSSFEAKPSGSVVEQAEGVECDFSPLLSGTPPQVYNFKRLVFTNC
NYNLTKLLSLFSVNDFTCSQISPAAIASNCYSSLILDYFSYPLSMKSDLS
VSSAGPISQFNYKQSFSNPTCLILATVPHNLTTITKPLKYSYINKCSRLL
SDDRTEVPQLVNANQYSPCVSIVPSTVWEDGDYYRKQLSPLEGGGWLVAS
GSTVAMTEQLQMGFGITVQYGTDTNSVCPKL SEQ ID NO. 6 [aa367-588 of MERS-CoV S protein]:
EAKPSGSVVEQAEGVECDFSPLLSGTPPQVYNFKRLVFTNCNYNLTKLLS
LFSVNDFTCSQISPAAIASNCYSSLILDYFSYPLSMKSDLSVSSAGPISQ
FNYKQSFSNPTCLILATVPHNLTTITKPLKYSYINKCSRLLSDDRTEVPQ
LVNANQYSPCVSIVPSTVWEDGDYYRKQLSPLEGGGWLVASGSTVAMTEQ
LQMGFGITVQYGTDTNSVCPKL SEQ ID NO. 7 [aa367-606 of MERS-CoV S protein]:
EAKPSGSVVEQAEGVECDFSPLLSGTPPQVYNFKRLVFTNCNYNLTKLLS
LFSVNDFTCSQISPAAIASNCYSSLILDYFSYPLSMKSDLSVSSAGPISQ
FNYKQSFSNPTCLILATVPHNLTTITKPLKYSYINKCSRLLSDDRTEVPQ
LVNANQYSPCVSIVPSTVWEDGDYYRKQLSPLEGGGWLVASGSTVAMTEQ
LQMGFGITVQYGTDTNSVCPKLEFANDTKIASQLGNCVEY SEQ ID NO. 8 [S350-588-Fc]:
SYESFDVESGVYSVSSFEAKPSGSVVEQAEGVECDFSPLLSGTPPQVYNF
KRLVFTNCNYNLTKLLSLFSVNDFTCSQISPAAIASNCYSSLILDYFSYP
LSMKSDLSVSSAGPISQFNYKQSFSNPTCLILATVPHNLTTITKPLKYSY
INKCSRLLSDDRTEVPQLVNANQYSPCVSIVPSTVWEDGDYYRKQLSPLE
GGGWLVASGSTVAMTEQLQMGFGITVQYGTDTNSVCPKLRSDKTHTCPPC
PAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVMH
EALHNHYTQKSLSLSPGK SEQ ID NO. 9 [S358-588-Fc]:
SGVYSVSSFEAKPSGSVVEQAEGVECDFSPLLSGTPPQVYNFKRLVFTNC
NYNLTKLLSLFSVNDFTCSQISPAAIASNCYSSLILDYFSYPLSMKSDLS
VSSAGPISQFNYKQSFSNPTCLILATVPHNLTTITKPLKYSYINKCSRLL
SDDRTEVPQLVNANQYSPCVSIVPSTVWEDGDYYRKQLSPLEGGGWLVAS
GSTVAMTEQLQMGFGITVQYGTDTNSVCPKLRSDKTHTCPPCPAPELLGG
PSVFLFPPKPKDTLMISRTPEVTCVVVDVSHEDPEVKFNWYVVDGVEVHNA
KTKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHYT
QKSLSLSPGK SEQ ID NO. 10 [S367-588-Fc]:
EAKPSGSVVEQAEGVECDFSPLLSGTPPQVYNFKRLVFTNCNYNLTKLLS
LFSVNDFTCSQISPAAIASNCYSSLILDYFSYPLSMKSDLSVSSAGPISQ
FNYKQSFSNPTCLILATVPHNLTTITKPLKYSYINKCSRLLSDDRTEVPQ
LVNANQYSPCVSIVPSTVWEDGDYYRKQLSPLEGGGWLVASGSTVAMTEQ
LQMGFGITVQYGTDTNSVCPKLRSDKTHTCPPCPAPELLGGPSVFLFPPK
PKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPG
K SEQ ID NO. 11 [S367-606-Fc]:
EAKPSGSVVEQAEGVECDFSPLLSGTPPQVYNFKRLVFTNCNYNLTKLLS
LFSVNDFTCSQISPAAIASNCYSSLILDYFSYPLSMKSDLSVSSAGPISQ
FNYKQSFSNPTCLILATVPHNLTTITKPLKYSYINKCSRLLSDDRTEVPQ
LVNANQYSPCVSIVPSTVWEDGDYYRKQLSPLEGGGWLVASGSTVAMTEQ
LQMGFGITVQYGTDTNSVCPKLEFANDTKIASQLGNCVEYRSDKTHTCPP
CPAPELLGGPSVFLFPPKPKDTLMISRTPEVTCVVVDVSHEDPEVKFNWY
VVDGVEVHNAKTKPREEQYNSTYRVVSVLTVLHQDWLNGKEYKCKVSNKA
LPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSV
MHEALHNHYTQKSLSLSPGK SEQ ID NO. 12 [S377-588-Fc]:
QAEGVECDFSPLLSGTPPQVYNFKRLVFTNCNYNLTKLLSLFSVNDFTCS
QISPAAIASNCYSSLILDYFSYPLSMKSDLSVSSAGPISQFNYKQSFSNP
TCLILATVPHNLTTITKPLKYSYINKCSRLLSDDRTEVPQLVNANQYSPC
VSIVPSTVWEDGDYYRKQLSPLEGGGWLVASGSTVAMTEQLQMGFGITVQ
YGTDTNSVCPKLRSDKTHTCPPCPAPELLGGPSVFLFPPKPKDTLMISRT
PEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFL
YSKLTVDKSRWQQGNVFSCSVMHEALHNHYTQKSLSLSPGK SEQ ID NO. 13 [S377-662-Fc]:
QAEGVECDFSPLLSGTPPQVYNFKRLVFTNCNYNLTKLLSLFSVNDFTCS
QISPAAIASNCYSSLILDYFSYPLSMKSDLSVSSAGPISQFNYKQSFSNP
TCLILATVPHNLTTITKPLKYSYINKCSRLLSDDRTEVPQLVNANQYSPC
VSIVPSTVWEDGDYYRKQLSPLEGGGWLVASGSTVAMTEQLQMGFGITVQ
YGTDTNSVCPKLEFANDTKIASQLGNCVEYSLYGVSGRGVFQNCTAVGVR
QQRFVYDAYQNLVGYYSDDGNYYCLRACVSVPVSVIRSDKTHTCPPCPAP
ELLGGPSVFLFPPKPKDTLMISRTPEVTCVVVDVSHEDPEVKFNVVYVDG
VEVHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEA
LHNHYTQKSLSLSPGK SEQ ID NO. 14 [Foldon (Fd)]:
GYIPEAPRDGQAYVRKDGEVVVLLSTFL SEQ ID NO. 15 [human IgG Fc (hFc)]:
RSDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCL
VKGFYPSDIAVEWESNGQPENNYKTTPPVLDSDGSFFLYSKLTVDKSRWQ
QGNVFSCSVMHEALHNHYTQKSLSLSPGK TABLE 1-continued Amino acid sequences of MERS-CoV regions and immunopotentiators SEQ ID NO. 16 [mouse IgG Fc (mFc)]:
RSPRGPTIKPCPPCKCPAPNLLGGPSVFIFPPKIKDVLMISLSPIVTCVV
VDVSEDDPDVQISWFVNNVEVHTAQTQTHREDYNSTLRVVSALPIQHQDW
MSGKEFKCKVNNKDLPAPIERTISKPKGSVRAPQVYVLPPPEEEMTKKQV
TLTCMVTDFMPEDIYVEWTNNGKTELNYKNTEPVLDSDGSYFMYSKLRVE
KKNWVERNSYSCSVVHEGLHNHHTTKSFSRTPGK SEQ ID NO. 17 [rabbit IgG Fc (rFc)]:
RSSKPTCPPPELLGGPSVFIFPPKPKDTLMISRTPEVTCVVVDVSQDDPE
VQFTWYINNEQVRTARPPLREQQFNSTIRVVSTLPIAHQDWLRGKEFKCK
VHNKALPAPIEKTISKARGQPLEPKVYTMGPPREELSSRSVSLTCMINGF
YPSDISVEWEKNGKAEDNYKTTPAVLDSDGSYFLYSKLSVPTSEWQRGDV
FTCSVMHEALHNHYTQKSISRSPGK SEQ ID NO. 18
[Human C3d (aa residues 1002-1303 in C3)]:
HLIVTPSGCGEQNMIGMTPTVIAVHYLDETEQWEKFGLEKRQGALELIKK
GYTQQLAFRQPSSAFAAFVKRAPSTWLTAYVVKVFSLAVNLIAIDSQVLC
GAVKWLILEKQKPDGVFQEDAPVIHQEMIGGLRNNNEKDMALTAFVLISL
QEAKDICEEQVNSLPGSITKAGDFLEANYMNLQRSYTVAIAGYALAQMGR
LKGPLLNKFLTTAKDKNRWEDPGKQLYNVEATSYALLALLQLKDFDFVPP
VVRWLNEQRYYGGGYGSTQATFMVFQALAQYQKDAPDHQELNLDVSLQLP
SR SEQ ID NO. 19 [Cholera toxin b subunit
(aa residues 1-124)]:
MTPQNITDLCAEYHNTQIHTLNDKIFSYTESLAGKREMAIITFKNGATFQ
VEVPGSQHIDSQKKAIERMKDTLRIAYLTEAKVEKLCVWNNKTPRAIAAI
SMAN Optionally, a trimerization stabilization sequence is disposed between the MERS-CoV sequence and the immunopotentiator. In one embodiment, the stabilization sequence comprises a sequence that stabilizes the RGB protein sequence in a trimer or oligomer configuration. As used herein, the terms stabilization sequence, trimeric motif, and trimerization sequence are interchangeable and equivalent. Suitable stabilization sequences include, but are not limited to, a 27 amino acid region of the C-terminal domain of T4 fibritin (a foldon-like sequence) (GYIPEAPRDGQAY-VRKDGEWVLLSTFL, SEQ ID NO. 14 or GSGYI-PEAPRDGQAYVRKDGE WVLLSTFL, SEQ ID NO. 20), a GCN4 (MKQIEDKIEEILSKIYHIENEIARIKKLIGEV; SEQ ID NO. 21), an IQ (RMKQIEDKIEEIESKQKKIENE-IARIKK; SEQ ID NO. 22), or an IZ (IKKEIEAIKKEQEAI KKKIEAIEK; SEQ ID NO. 23). Other suitable stabilization methods include, but are not limited to, 2,2-bipyridine-5-carboxylic acid (BPY), disulfide bonds and facile ligation.

In another embodiment, the immunopotentiator comprises a sequence to enhance the immunogenicity of the immunogenic composition. Suitable immunopotentiators include, but are not limited to, an Fc fragment of human IgG, a C3d (a complement fragment that promotes antibody formation binding to antigens enhancing their uptake by dendritic cells and B cells) (SEQ ID NO:18), an Ov ASP-1 (*Onchocerca volvulus* homologue of the activation associated secreted gene family) (see US 20060039921, which is incorporated by reference herein for all it discloses regarding ASP-1 adjuvants), a cholera toxin (SEQ ID NO:19), a muramyl peptide, and a cytokine.

In one embodiment, the immunopotentiator is an immunoglobulin Fc fragment. The immunoglobulin molecule consists of two light (L) chains and two heavy (H) chains held together by disulfide bonds such that the chains form a Y shape. The base of the Y (carboxyl terminus of the heavy chain) plays a role in modulating immune cell activity. This region is called the Fc region, and is composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins. By doing this, it mediates different physiological effects including opsonization, cell lysis, and degranulation of mast cells, basophils, and eosinophils.

Figure 1:
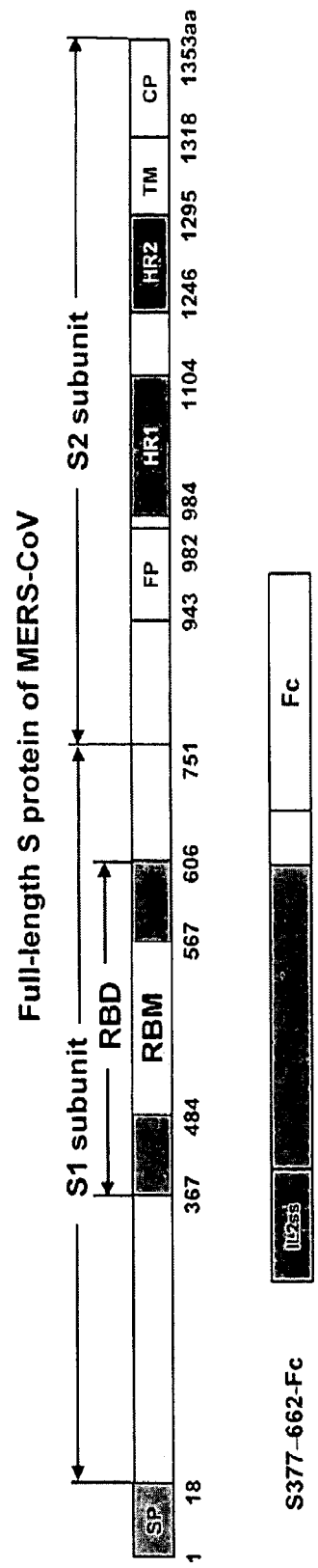
FIG. 1 depicts the schematic representation of spike (S) protein of Middle East respiratory syndrome coronavirus (MERS-CoV) and the recombinant S377-662-Fc (human IgG Fc) protein. The MERS-CoV S protein includes the following functional domains in the S1 and S2: signal peptide (SP), receptor-binding domain (RBD), receptor-binding motif (RBM), fusion peptide (FP), heptad repeat 1 (HR1), heptad repeat 2 (HR2), transmembrane domain (TM), and cytoplasm domain (CP).

Exemplary subunit MERS-CoV immunogenic compositions are found in FIG. 1. In certain embodiments, the coronavirus and immunopotentiator portions of the fusion protein are linked through a flexible linker comprising $(GGGGS)_n$ (SEQ ID NO:24), wherein n is an integer between 0 and 8. In certain embodiments, n is 0, n is 1, n is 2, n is 3, n is 4, n is 5, n is 6, n is 7, or n is 8.

The disclosed MERS-CoV immunogenic compositions include conservative variants of the proteins. A conservative variant refers to a peptide or protein that has at least one amino acid substituted by another amino acid, or an amino acid analog, that has at least one property similar to that of the original amino acid from an exemplary reference peptide. Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative substitution can be assessed by a variety of factors, such as, e.g., the physical properties of the amino acid being substituted (Table 1) or how the original amino acid would tolerate a substitution (Table 2). The selections of which amino acid can be substituted for another amino acid in a peptide disclosed herein are known to a person of ordinary skill in the art. A conservative variant can function in substantially the same manner as the exemplary reference peptide, and can be substituted for the exemplary reference peptide in any aspect of the present specification.

TABLE 1

Amino Acid Properties

| Property | Amino Acids |
| --- | --- |
| Aliphatic | G, A, I, L, M, P, V |
| Aromatic | F, H, W, Y |
| C-beta branched | I, V, T |
| Hydrophobic | C, F, I, L, M, V, W |
| Small polar | D, N, P |
| Small non-polar | A, C, G, S, T |
| Large polar | E, H, K, Q, R, W, Y |
| Large non-polar | F, I, L, M, V |
| Charged | D, E, H, K, R |
| Uncharged | C, S, T |
| Negative | D, E |
| Positive | H, K, R |
| Acidic | D, E |
| Basic | K, R |
| Amide | N, Q |

TABLE 2

Amino Acid Substitutions

| Amino Acid | Favored Substitution | Neutral Substitutions | Disfavored substitution |
|---|---|---|---|
| A | G, S, T | C, E, I, K, M, L, P, Q, R, V | D, F, H, N, Y, W |
| C | F, S, Y, W | A, H, I, M, L, T, V | D, E, G, K, N, P, Q, R |
| D | E, N | G, H, K, P, Q, R, S, T | A, C, I, L, |
| E | D, K, Q | A, H, N, P, R, S, T | C, F, G, I, L, M, V, W, Y |
| F | M, L, W, Y | C, I, V | A, D, E, G, H, K, N, P, Q, R, S, T |
| G | A, S | D, K, N, P, Q, R | C, E, F, H, I, L, M, T, V, W, Y |
| H | N, Y | C, D, E, K, Q, R, S, T, W | A, F, G, I, L, M, P, V |
| I | V, L, M | A, C, T, F, Y | D, E, G, H, K, N, P, Q, R, S, W |
| K | Q, E, R | A, D, G, H, M, N, P, S, T | C, F, I, L, V, W, Y |
| L | F, I, M, V | A, C, W, Y | D, E, G, H, K, N, P, Q, R, S, T |
| M | F, I, L, V | A, C, R, Q, K, T, W, Y | D, E, G, H, N, P, S |
| N | D, H, S | E, G, K, Q, R, T | A, C, F, I, L, M, P, V, W, Y |
| P | - | A, D, E, G, K, Q, R, S, T | C, F, H, I, L, M, N, V, W, Y |
| Q | E, K, R | A, D, G, H, M, N, P, S, T | C, F, I, L, V, W, Y |
| R | K, Q | A, D, E, G, H, M, N, P, S, T | C, F, I, L, V, W, Y |
| S | A, N, T | C, D, E, G, H, K, P, Q, R, T | F, I, L, M, V, W, Y |
| T | S | A, C, D, E, H, I, K, M, N, P, Q, R, V | F, G, L, W, Y |
| V | I, L, M | A, C, F, T, Y | D, E, G, H, K, N, P, Q, R, S, W |
| W | F, Y | H, L, M | A, C, D, E, G, I, K, N, P, Q, R, S, T, V |
| Y | F, H, W | C, I, L, M, V | A, D, E, G, K, N, P, Q, R, S, T |

Matthew J. Betts and Robert, B. Russell, Amino Acid Properties and Consequences of Substitutions, pp. 289-316, In Bio informatics for Geneticists, (eds Michael R. Barnes, Ian C. Gray, Wiley, 2003).

An MERS-CoV immunogenic composition can also comprise conservative variants to the disclosed proteins. In aspects of this embodiment, a conservative variant of an MERS-CoV immunogenic composition can be, for example, an amino acid sequence having at least 75%, at least 80%, at least 85%, at least 90%, at least 95%, at least 97%, at least 98%, or at least 99% amino acid sequence identity to the MERS-CoV immunogenic compositions disclosed herein. In other aspects of this embodiment, a conservative variant of an MERS-CoV immunogenic composition can be, for example, an amino acid sequence having at most 75%, at most 80%, at most 85%, at most 90%, at most 95%, at most 97%, at most 98%, or at most 99% amino acid sequence identity to the MERS-CoV immunogenic compositions disclosed herein.

In other embodiments, the MERS-CoV S protein sequence comprises an amino acid sequence having at least 75%, at least 80%, at least 85%, at least 90%, at least 95%, at least 97%, at least 98%, or at least 99% amino acid sequence identity to the MERS-CoV S amino acid sequences of any of SEQ ID NOs.1-7.

In still other embodiments, the immunopotentiator sequence comprises an amino acid sequence having at least 75%, at least 80%, at least 85%, at least 90%, at least 95%, at least 97%, at least 98%, or at least 99% amino acid sequence identity to the immunopotentiator amino acid sequences of any of SEQ ID NOs. 9-11, 17 or 18.

In other aspects of this embodiment, a conservative variant of an MERS-CoV immunogenic composition, a MERS-CoV S protein amino acid sequence, or an immunopotentiator amino acid sequence can have, for example, 1, 2, 3, 4, 5, 6, 7, 8, 9, 10, 11, 12, 13, 14, 15, or more conservative substitutions, to the amino acid sequence of the MERS-CoV immunogenic compositions, MERS-CoV S protein, or immunopotentiator disclosed herein. In other aspects of this embodiment, a conservative variant of an MERS-CoV immunogenic composition, a MERS-CoV S protein amino acid sequence, or an immunopotentiator amino acid sequence can be, for example, an amino acid sequence having at least 1, at least 2, at least 3, at least 4, at least 5, at least 6, at least 7, at least 8, at least 9, at least 10, at least 11, at least 12, at least 13, at least 14, or at least 15 conservative substitutions to the amino acid sequence of the MERS-CoV immunogenic compositions, MERS-CoV S protein, or immunopotentiator disclosed herein. In yet other aspects of this embodiment, a conservative variant of an MERS-CoV immunogenic composition, a MERS-CoV S protein amino acid sequence, or an immunopotentiator amino acid sequence can be, for example, an amino acid sequence having at most 1, at most 2, at most 3, at most 4, at most 5, at most 6, at most 7, at most 8, at most 9, at most 10, at most 11, at most 12, at most 13, at most 14, or at most 15 conservative substitutions to the amino acid sequence of the MERS-CoV immunogenic compositions, MERS-CoV S protein, or immunopotentiator disclosed herein. In further aspects of this embodiment, a conservative variant of an MERS-CoV immunogenic composition, a MERS-CoV S protein amino acid sequence, or an immunopotentiator amino acid sequence can be, for example, an amino acid sequence having from 1 to 15, 2 to 15, 3 to 15, 4 to 15, 5 to 15, 6 to 15, 7 to 15, 1 to 12, 2 to 12, 3 to 12, 4 to 12, 5 to 12, 6 to 12, 7 to 12, 1 to 10, 2 to 10, 3 to 10, 4 to 10, 5 to 10, 6 to 10, 7 to 10, 1 to 8, 2 to 8, 3 to 8, 4 to 8, 5 to 8, 6 to 8, 1 to 6, 2 to 6, 3 to 6, 4 to 6, 1 to 4, 2 to 4, or 1 to 3 conservative substitutions to the amino acid sequence of the MERS-CoV immunogenic compositions, MERS-CoV S protein, or immunopotentiator disclosed herein.

Expression systems such as the following are suitable for use in expressing the disclosed fusion proteins: mammalian cell expression systems such as, but not limited to, the pcDNA and GS Gene expression systems; insect cell expression systems such as, but not limited to, Bac-to-Bac, baculovirus, and DES expression systems; and *E. coli* expression systems including, but not limited to, pET, pSUMO, and GST expression systems.

Various advantages are associated with expression of proteins in mammalian cell expression systems. The mammalian cell expression system is a relatively mature eukaryotic system for expression of recombinant proteins. It is more likely to achieve a correctly folded soluble protein with proper glycosylation, making the expressed protein maintain its native conformation and keep sufficient bioactivity. This system can either transiently or stably express recombinant antigens, and promote signal synthesis. Recombinant proteins expressed in this way may maintain proper antigenicity and immunogenicity. However, both insect and bacterial expression systems provide inexpensive and efficient expression of proteins, which may be appropriate under certain conditions.

The purification systems used to purify the recombinant proteins are dependent on whether a tag is linked or fused with the coronavirus sequence. If the fusion proteins are fused with IgG Fc, Protein A, or Protein G, affinity chromatography is used for the purification. If the fusion proteins are fused with GST proteins, the GST columns will be used for the purification. If the fusion proteins link with 6×His tag at the N- or C-terminal, the expressed proteins are to be purified using His tag columns. If no tag is linked with the fusion protein, the expressed protein could be purified using fast protein liquid chromatography (FPLC), high performance liquid chromatography (HPLC), or other chromatography.

In certain embodiments, the immunogenic compositions further comprise or are administered with an adjuvant. Adjuvants suitable for use in animals include, but are not limited to, Freund's complete or incomplete adjuvants, Sigma Adjuvant System (SAS), and Ribi adjuvants. Adjuvants suitable for use in humans include, but are not limited to, MF59 (an oil-in-water emulsion adjuvant); Montanide ISA 51 or 720 (a mineral oil-based or metabolizable oil-based adjuvant); aluminum hydroxide, -phosphate, or -oxide; HAVLOGEN® (an acrylic acid polymer-based adjuvant, Intervet Inc., Millsboro, Del.); polyacrylic acids; oil-in-water or water-in-oil emulsion based on, for example a mineral oil, such as BAYOL™ or MARCOL™ (Esso Imperial Oil Limited, Canada), or a vegetable oil such as vitamin E acetate; saponins; and *Onchocerca volvulus* activation-associated protein-1 (Ov ASP-1) (see US 20060039921, which is incorporated by reference herein for all it discloses regarding Ov ASP-1 adjuvants). However, components with adjuvant activity are widely known and, generally, any adjuvant may be utilized that does not adversely interfere with the efficacy or safety of the vaccine and/or immunogenic composition.

Vaccines and/or immunogenic compositions according to the various embodiments disclosed herein can be prepared and/or marketed in the form of a liquid, frozen suspension, or in a lyophilized form. Typically, vaccines and/or immunogenic compositions prepared according to the present disclosure contain a pharmaceutically acceptable carrier or diluent customarily used for such compositions. Carriers include, but are not limited to, stabilizers, preservatives, and buffers. Suitable stabilizers are, for example SPGA, Tween compositions (such as are available from A.G. Scientific, Inc., San Diego, Calif.), carbohydrates (such as sorbitol, mannitol, starch, sucrose, dextran, glutamate, or glucose), proteins (such as dried milk serum, albumin, or casein), or degradation products thereof. Examples of suitable buffers include alkali metal phosphates. Suitable preservatives include thimerosal, merthiolate, and gentamicin. Diluents include water, aqueous buffer (such as buffered saline), alcohols, and polyols (such as glycerol).

Also disclosed herein are methods for inducing an immune response to a MERS-CoV using the disclosed proteins. Generally, the vaccine and/or immunogenic composition may be administered subcutaneously, intradermally, submucosally, intranasally, or intramuscularly in an effective amount to prevent infection from the MERS-CoV and/or treat an infection from the MERS-CoV. An effective amount to prevent infection is an amount of immunizing protein that will induce immunity in the immunized animals against challenge by a virulent virus such that infection is prevented or the severity is reduced. Immunity is defined herein as the induction of a significant higher level of protection in a subject after immunization compared to an unimmunized group. An effective amount to treat an infection is an amount of immunizing protein that induces an appropriate immune response against MERS-CoV such that severity of the infection is reduced.

Protective immune responses can include humoral immune responses and cellular immune responses. Protection against MERS-CoV is believed to be conferred through serum antibodies (humoral immune response) directed to the surface proteins, with mucosal IgA antibodies and cell-mediated immune responses also playing a role. Cellular immune responses are useful in protection against MERS-CoV virus infection with CD4+ and CD8+ T cell responses being particularly important. CD8+ immunity is of particular importance in killing virally infected cells.

Additionally, the disclosed proteins and/or immunogenic compositions can be administered using immunization schemes known by persons of ordinary skill in the art to induce protective immune responses. These include a single immunization or multiple immunizations in a prime-boost strategy. A boosting immunization can be administered at a time after the initial, prime, immunization that is days, weeks, months, or even years after the prime immunization. In certain embodiments, a boost immunization is administered 2 weeks, 1 month, 2, months, 3 months, 4 months, 5 months, or 6 months or more after the initial prime immunization. Additional multiple boost immunizations can be administered such as weekly, every other week, monthly, every other month, every third month, or more. In other embodiments, the boost immunization is administered every 3 weeks, every 4 weeks, every 5 weeks, every 6 weeks, every 7 weeks, every 8 weeks, every 9 weeks, every 10 weeks, every 11 weeks, or every 12 weeks. In certain embodiments, boosting immunizations can continue until a protective anti-MERS-CoV antibody titer is seen in the subject's serum. In certain embodiments, a subject is given one boost immunization, two boost immunizations, three boost immunizations, or four or more boost immunizations, as needed to obtain a protective antibody titer. In other embodiments, the adjuvant in the initial prime immunization and the adjuvant in the boost immunizations are different.

Further, in various formulations of the proteins and/or immunogenic compositions, suitable excipients, stabilizers, and the like may be added as are known by persons of ordinary skill in the art.

The disclosed proteins, immunogenic compositions, and methods may be used to prevent MERS-CoV virus infection in a subject susceptible thereto such as, but not limited to, a human, a primate, a domesticated animal, an animal in the wild, or a bird.

EXAMPLES

Example 1

Materials and Methods

Construction, Expression, and Purification of Recombinant Proteins.

The construction, expression, and purification of the recombinant protein fused with Fc (S350-588-Fc, S358-588-Fc, S367-588-Fc, S367-606-Fc, S377-588-Fc, and S377-662-Fc) were done as follows. Briefly, genes encoding residues 350-588, 358-588, 367-588, 367-606, 377-588, or 377-662 of MERS-CoV S protein were amplified by PCR using synthesized codon-optimized MERS-CoV S sequences (GenBank: AFS88936.1) as the template. These fragments were then digested by EcoRl and BglII restriction enzymes and inserted into the pFUSE-hIgG1-Fc2 expression vector (hereinafter named Fc). The sequence-confirmed recombinant plasmids were respectively transfected into 293T cells which had been seeded 24 hr before transfection, followed by replacing culture medium with serum-free DMEM 8-10 hr later, and collection of supernatant containing expressed protein 72 hr post-transfection. The recombinant S350-588-Fc, S358-588-Fc, S367-588-Fc, S367-606-Fc, S377-588-Fc, and S377-662-Fc proteins were then purified by Protein A affinity chromatography.

SDS-PAGE and Western Blot.

The purified proteins were analyzed by SDS-PAGE and Western blot. Briefly, the proteins were either boiled at 95° C. for 5 min or not boiled, and separated by 10% Tris-Glycine gel. The proteins were then stained with Coomassie Blue or transferred to nitrocellulose membranes for Western blot analysis. After blocking with 5% non-fat milk in PBST overnight at 4° C., the blots were incubated for 1 hr at room temperature with MERS-CoV S1-specific polyclonal antibodies (1:1,000). After three washes, the blots were then incubated with horseradish peroxidase (HRP)-conjugated goat anti-mouse IgG (1:5,000) for 1 hr at room temperature. Signals were visualized with ECL Western blot substrate reagents and Amersham Hyperfilm.

Mouse Immunization and Sample Collection.

Mice were prime-immunized s.c. with 10 µg/mouse of recombinant S350-588-Fc, S358-588-Fc, S367-588-Fc, S367-606-Fc, S377-588-Fc, or S377-662-Fc protein formulated with Montanide ISA 51 adjuvant, or i.n. with 10 µg/mouse of recombinant S377-662-Fc formulated with poly(I:C) adjuvant. Both groups were boosted with 10 µg/mouse of the same immunogen and adjuvant at 3-week intervals. Sera were collected at 10 days post-last immunization to detect MERS-CoV S1-specific IgG antibodies and neutralizing antibodies.

ELISA.

Collected mouse sera were analyzed for MERS-CoV or SARS-CoV S-specific antibody responses by ELISA. Briefly, 96-well ELISA plates were respectively precoated with recombinant proteins overnight at 4° C. and blocked with 2% non-fat milk for 2 hr at 37° C. Serially diluted mouse sera or monoclonal antibodies (mAbs) were added to the plates and incubated at 37° C. for 1 hr, followed by four washes. Bound antibodies were incubated with HRP-conjugated goat anti-mouse IgG (1:2,000) for 1 hr at 37° C. The reaction was visualized by substrate 3,3',5,5'-tetramethylbenzidine (TMB) and stopped by 1 N $H_2SO_4$. The absorbance at 450 nm (A450) was measured by ELISA plate reader.

Live Virus-Based Neutralization Assay.

Neutralizing antibody titers of mouse sera against infection by live MERS-CoV or SARS-CoV were further detected as described below. Briefly, serial 2-fold dilutions of mouse sera or mAbs were incubated with 100 $TCID_{50}$ (50% tissue culture infective dose) of MERS-CoV or SARS-CoV for 1 hr at 37° C. prior to addition to a monolayer of fetal rhesus monkey kidney (FRhK4) cells for SARS-CoV and Vero E6 cells for MERS-CoV in triplicate. Virus supernatant was removed and replaced with fresh medium after 1 hr of culture at 37° C. The cytopathic effect (CPE) in each well was observed daily and recorded on day 3 post-infection. The neutralizing titers of mouse antisera that completely prevented CPE in 50% of the wells ($NT_{50}$) were calculated.

Pseudovirus-Based Neutralization Assay.

An MERS-CoV pseudovirus neutralization assay was also established for detection of neutralizing activity induced by MERS-CoV RBD-Fc protein-immunized mouse sera against MERS-CoV infection. Briefly, a plasmid expressing codon-optimized MERS-CoV (hCoV-EMC, GenBank: AFS88936.1) genes was cotransfected with a plasmid encoding Env-defective, luciferase-expressing HIV-1 genome (pNL4-3.luc.RE) into 293T cells to collect pseudovirus in supernatants. Pseudovirus-containing supernatant was incubated with serially diluted mouse sera at 37° C. for 1 hr before adding to the target Huh-7 cells. Fresh medium was added 24 hr later, and the culture was continued for 72 hr. Cells were lysed by cell lysis buffer and transferred to 96-well luminometer plates. Luciferase substrate was added, and relative luciferase activity was determined by Ultra 384 luminometer. The neutralization of MERS-CoV S pseudovirus was presented as $NT_{50}$.

Results

Figure 2:
FIG. 2 depicts the SDS-PAGE and Western blot analysis of the expressed protein S377-662-Fc. The protein molecular weight marker (kDa) is indicated on the left. Antisera from mice immunized with S377-662-Fc were used for Western blot analysis.
Figure 3:
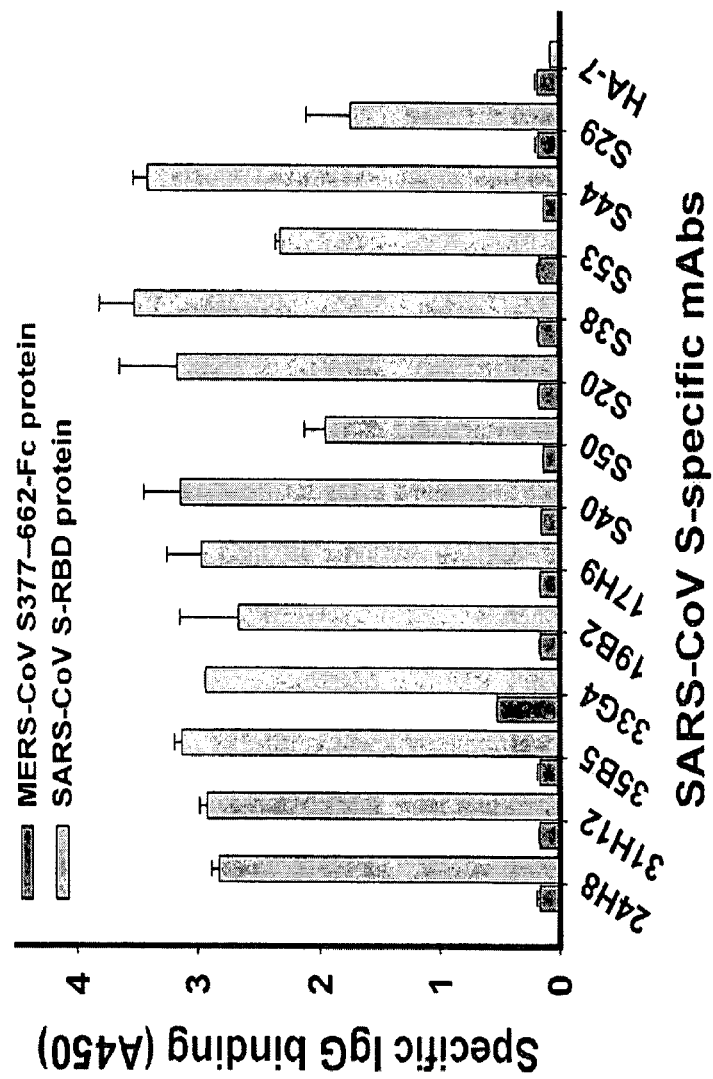
FIG. 3 depicts the binding of a series of severe acute respiratory syndrome (SARS) S protein-specific mAbs (1 µg/ml) to MERS-CoV S377-662-Fc protein and SARS-CoV S-RBD protein. The HA-7 mAb specific for the hemagglutinin (HA1) of H5N1 virus was used as an unrelated mAb control. The data are presented as mean A450±standard deviation (SD) of duplicate wells.

MERS-CoV S protein was expressed and its reactivity was tested with a variety of SARS-CoV S protein-specific monoclonal antibodies (mAbs) including 24H8, 31H12, 35B5, 33G4, 19B2, 17H9, S40, S50, S20, S38, S53, S44, and S29 (He, et al., J. Immunol. 174:4908-15, 2005; He, et al., Vaccine 24:5498-508, 2006, which are incorporated by reference herein for all they disclose regarding SARS-CoV S protein-specific MAbs). An antibody to the HA1 domain of influenza H5N1 virus, HA-7, was used as a control. Purified S377-662-Fc protein was expressed in soluble forms in the culture supernatant of transfected 293T cells, maintaining high expression with good purity (FIG. 2, left). This protein could be recognized by MERS-CoV S1-specific polyclonal antibodies, as detected by Western blot (FIG. 2, right). The expressed S377-662-Fc has a lower OD450 value (most antibodies have an OD450 value less 0.2) when tested by ELISA using S-specific SARS mAbs, with similar reactivity to the control HA-7 mAb (FIG. 3). These data suggest that S377-662-Fc is highly specific to the S protein of MERS-CoV, and that it maintains lower or no cross-reactivity with the majority of SARS-CoV S-specific mAbs.

Figures 4A, 4B:
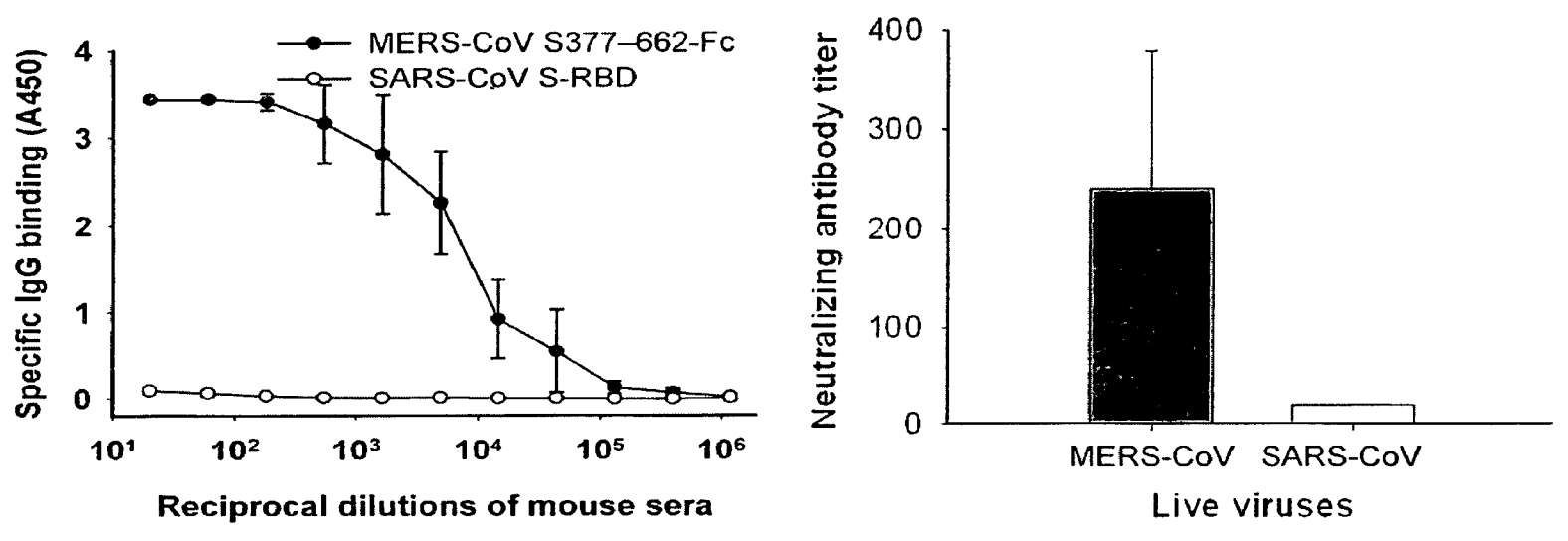

Next, the ability of expressed MERS-CoV S377-662-Fc protein to induce antibody responses, particularly neutralizing antibodies, was tested, and the ability of S377-662-Fc to elicit cross-reactivity and cross-neutralizing activity with SARS-CoV was evaluated. Mice were immunized with MERS-CoV S377-662-Fc, and then mouse sera were collected for the detection. MERS-CoV S377-662-Fc induced IgG antibodies against the S protein of MERS-CoV after the 2$^{nd}$ dose of immunogenic composition, which was confirmed by coating of the ELISA plates with an MERS-CoV S-specific protein not fused to Fc (MERS-CoV S377-662) (FIG. 4A). The MERS-CoV S-specific antibodies have low or no reactivity with a recombinant RBD protein of SARS- CoV used in development of a subunit SARS candidate vaccine (FIG. 4A). Nevertheless, the anti-MERS-CoV-S antibodies could neutralize live MERS-CoV infection in cell cultures in vitro, as detected by a MERS-CoV neutralization assay (FIG. 4B). However, the ability of the MERS-CoV S-specific antibodies to neutralize live SARS-CoV infection is very low (<1:40). The above data suggest that MERS-CoV has low to no cross-reactivity and cross-neutralizing activity with SARS-CoV.

Figure 5:
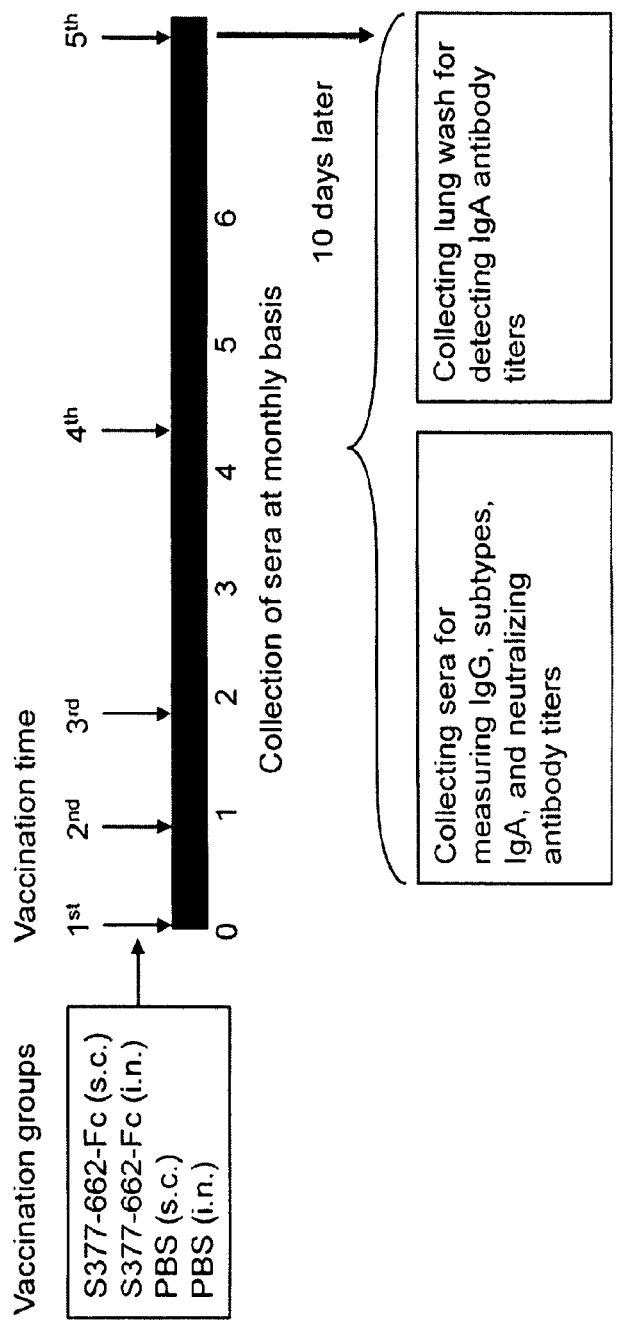
FIG. 5 depicts mouse immunization, sample collection, and immune response detection strategy. Four groups of mice were immunized subcutaneously (s.c.) or intranasally (i.n.) with MERS-CoV S377-662-Fc protein plus Montanide ISA51 (for s.c.) or poly(I:C) (for i.n.) adjuvant, or with PBS plus the corresponding adjuvant as their respective controls. Mouse sera and lung wash were collected as indicated and analyzed for humoral and mucosal immune responses and neutralization against MERS-CoV virus.
Figure 6B:
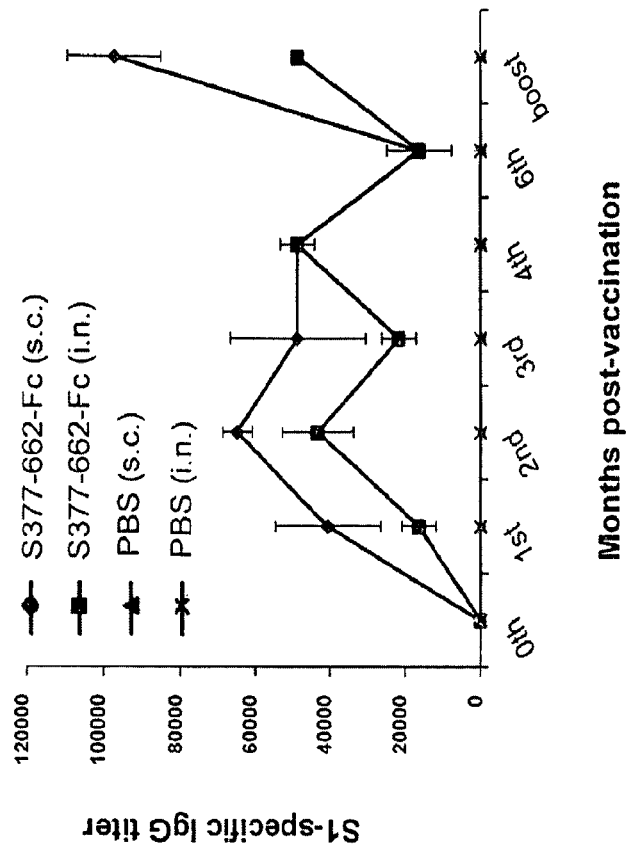
FIG. 6A and FIG. 6B depict the IgG antibody responses in sera of mice immunized (s.c. and i.n.) with MERS-CoV S377-662-Fc protein.
Figure 6A:
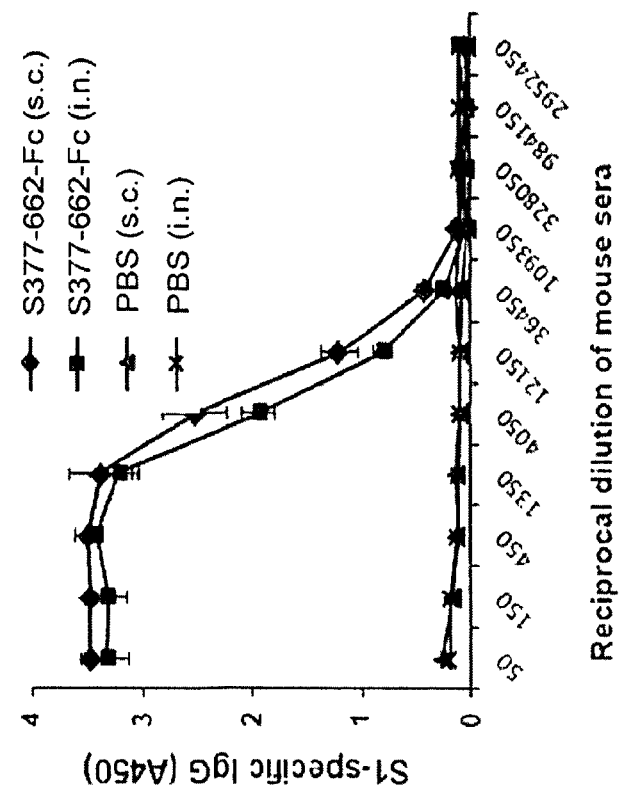
Figure 7B:
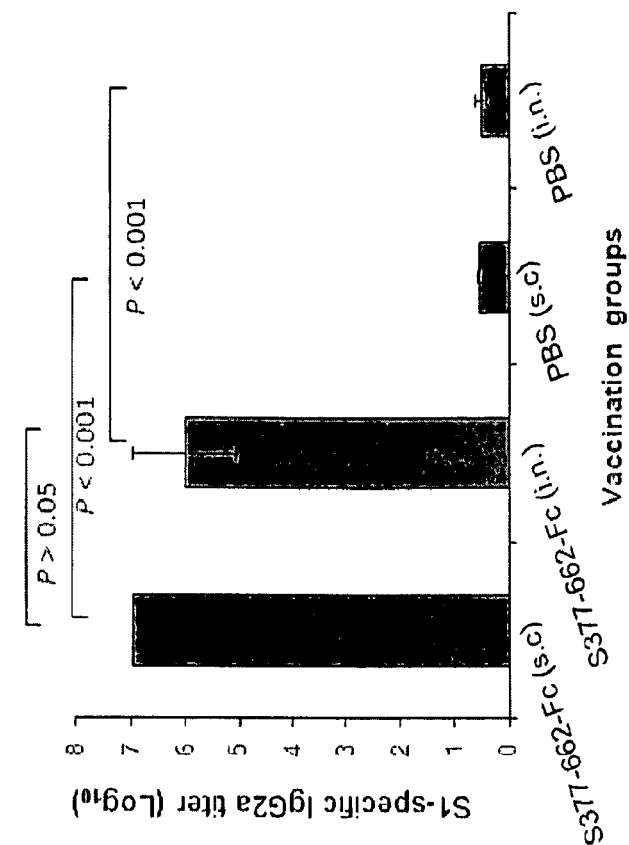
FIG. 7A and FIG. 7B depict the IgG subtypes in sera of mice immunized (s.c. and i.n.) with MERS-CoV S377-662-Fc protein. Binding of IgG1 (FIG. 7A) and IgG2a (FIG. 7B) to MERS-CoV S1-His protein is shown. Sera from 10 days post-last immunization were used for the detection, and the data are presented as geometric mean titer (GMT, endpoint titers)±SD of five mice per group. P<0.001 indicates significant difference.
Figure 7A:
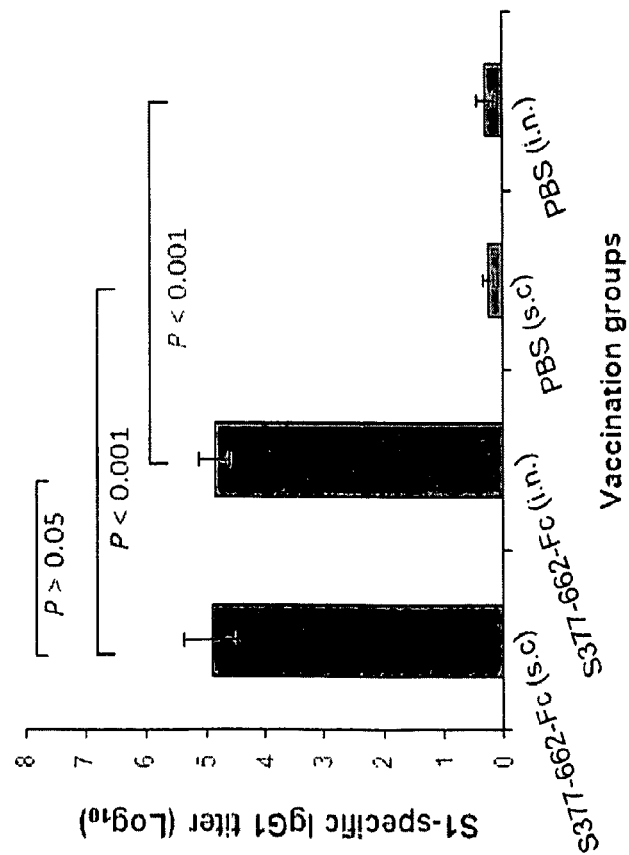
Figure 8B:
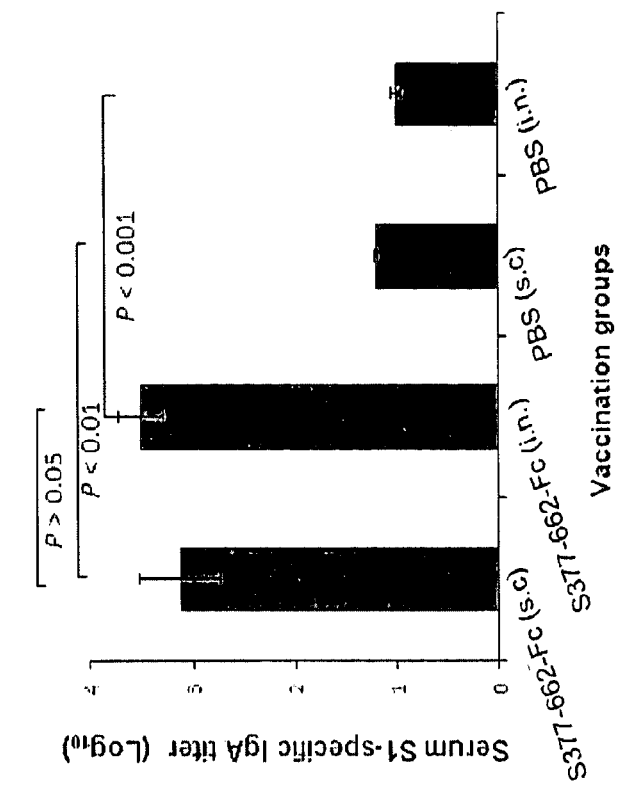
FIG. 8A and FIG. 8B depict the IgA antibody responses in lung wash and sera of mice immunized (s.c. and i.n.) with MERS-CoV S377-662-Fc protein. Binding of IgA in lung wash (1:1,000) (FIG. 8A) or sera (FIG. 8B) to MERS-CoV S1-His protein is shown. Samples from 10 days post-last immunization were used for the detection, and the data are presented as mean A450±SD (lung wash) or mean (GMT endpoint titers)±SD (sera) of five mice per group. P<0.05 indicates significant difference.
Figure 8A:
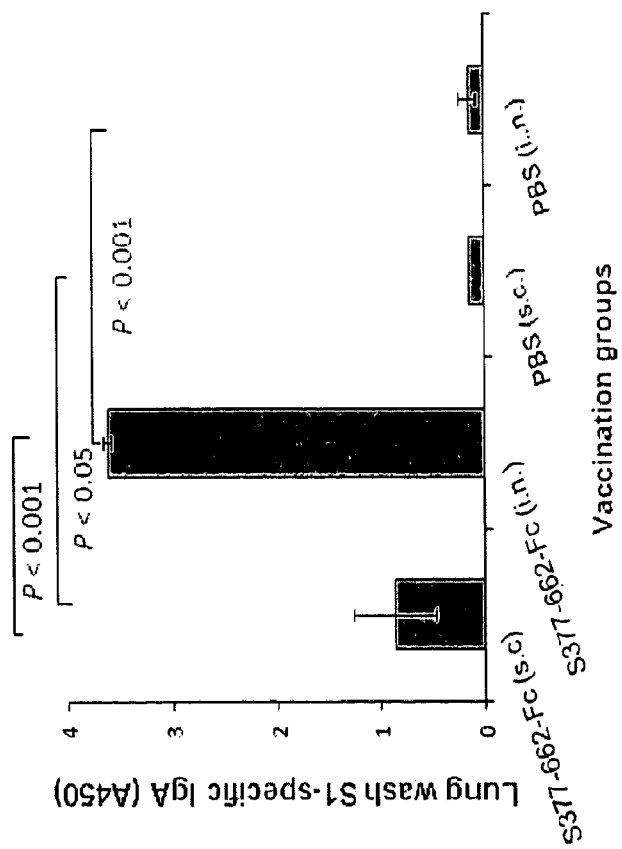

The systemic and mucosal immune responses induced by MERS-CoV RBD-Fc protein were further evaluated by immunizing mice with S377-662-Fc protein via the i.n. and s.c. immunization routes, and then detecting MERS-CoV S-specific IgG and IgA antibodies in immunized mouse sera and lung wash (FIG. 5). Indeed, sera from mice immunized via both administration routes could bind specifically to MERS-CoV S1-His protein, with the i.n. pathway inducing strong systemic humoral IgG antibody response similar to that of s.c. immunization (FIG. 6A). In addition, like the s.c. route, i.n. immunization with S377-662-Fc was able to stimulate long-term humoral immune responses in immunized mice through multiple boost immunizations, capable of maintaining protection for at least 6 months during the detection period (FIG. 6B). Furthermore, MERS-CoV S1-specific IgG1 (Th2-associated) and IgG2a (Th1-associated) antibody responses induced by the i.n. pathway were similar to those by the s.c. immunization (P>0.05), with a relatively higher level of IgG2a (Th1-associated) than IgG1 (Th2-associated) antibody against MERS-CoV S1 protein (FIG. 7), suggesting that MERS-CoV S377-662-Fc induced a slightly biased Th1-associated antibody response. Importantly, the i.n. immunization pathway induced similarly high level of IgA antibody to the s.c. route with equally strong neutralizing antibody responses against MERS-CoV in immunized mouse sera (P>0.05) (FIGS. 8B and 9A), but with a significantly higher level of IgA antibody with neutralizing activity than the s.c. route in mouse lungs (FIGS. 8A and 9B), indicating the ability of MERS-CoV S377-662-Fc protein in the induction of strong local mucosal immune response.

Figures 10A, 10B:
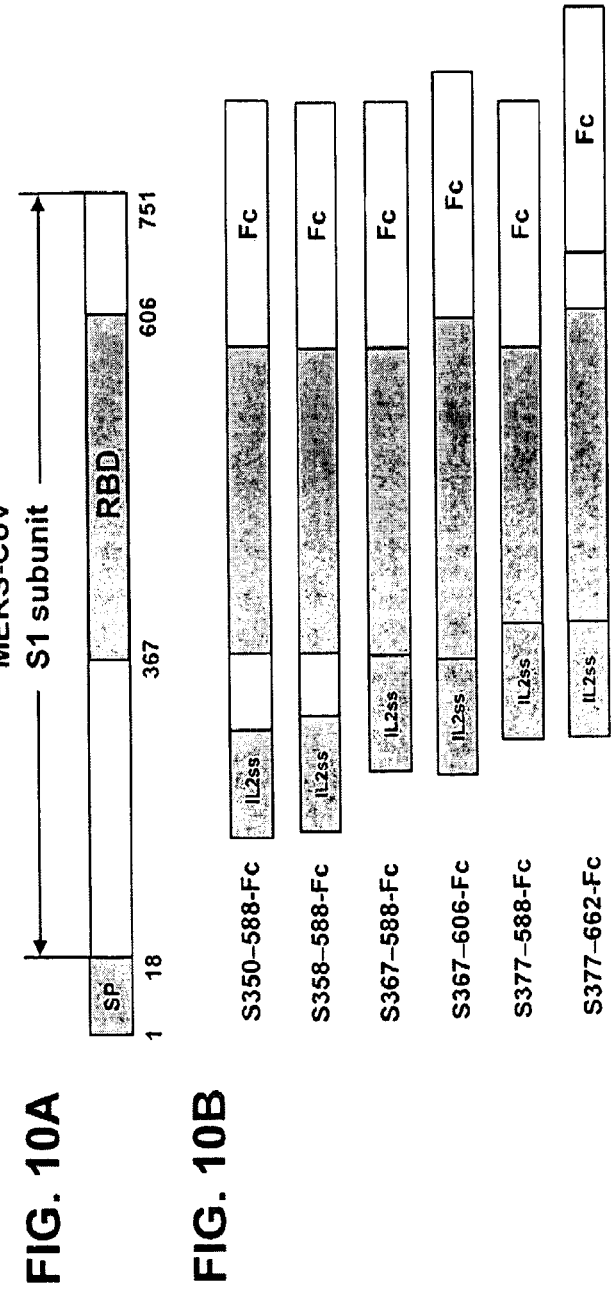
FIG. 10A and FIG. 10B depict a schematic representation of the S1 subunit of MERS-CoV (FIG. 10A) and recombinant proteins containing various fragments of the RBD domain of MERS-CoV S protein (FIG. 10B). Recombinant proteins S350-588-Fc, S358-588-Fc, S367-588-Fc, S367-606-Fc, and S377-588-Fc were constructed by inserting the corresponding RBD fragments into Fc of human IgG, and compared with S377-662-Fc.
Figures 11A, 11B:
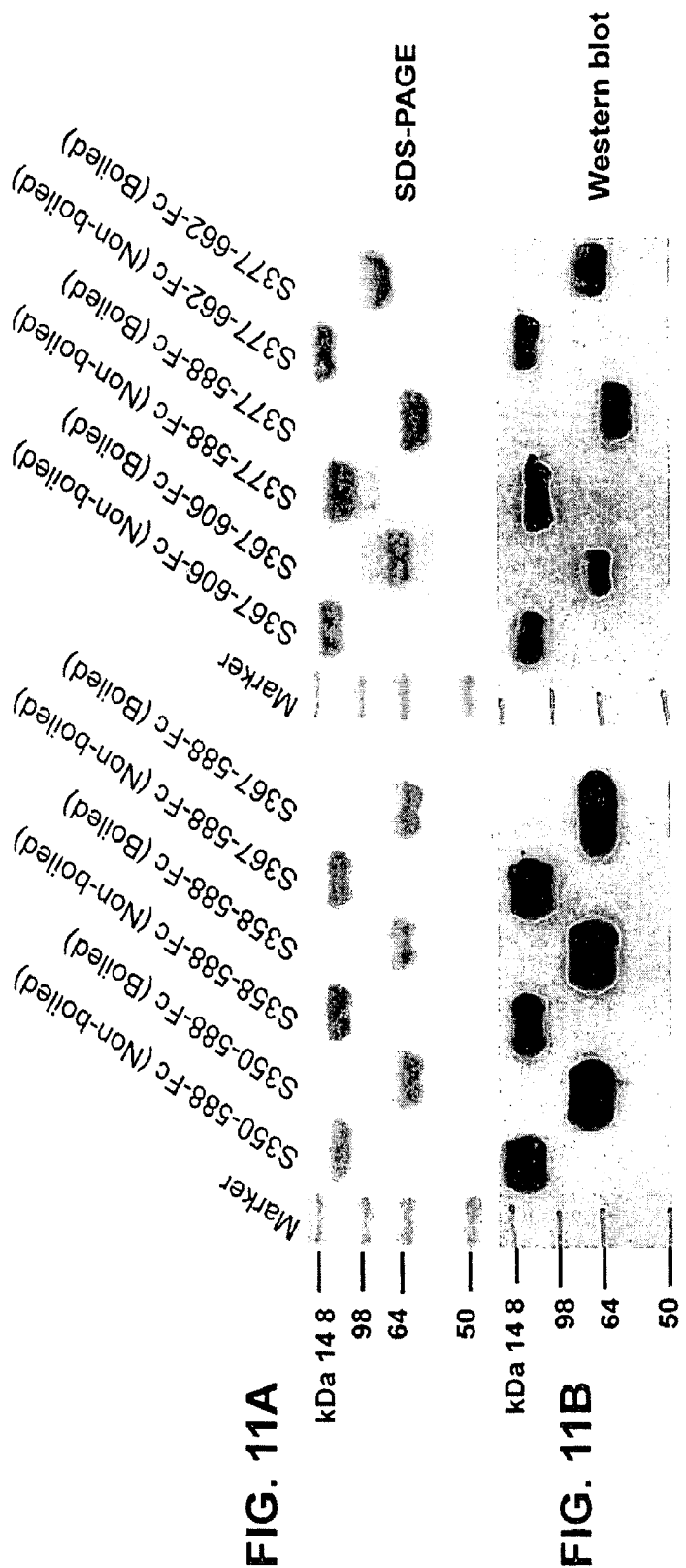
FIG. 11A and FIG. 11B depict the SDS-PAGE (FIG. 11A) and Western blot (FIG. 11B) analysis of the expressed MERS CoV RBD-Fc proteins. The protein molecular weight marker (kDa) is indicated on the left. Antisera from mice immunized with MERS-CoV S1-His were used for Western blot analysis.
Figure 12A:
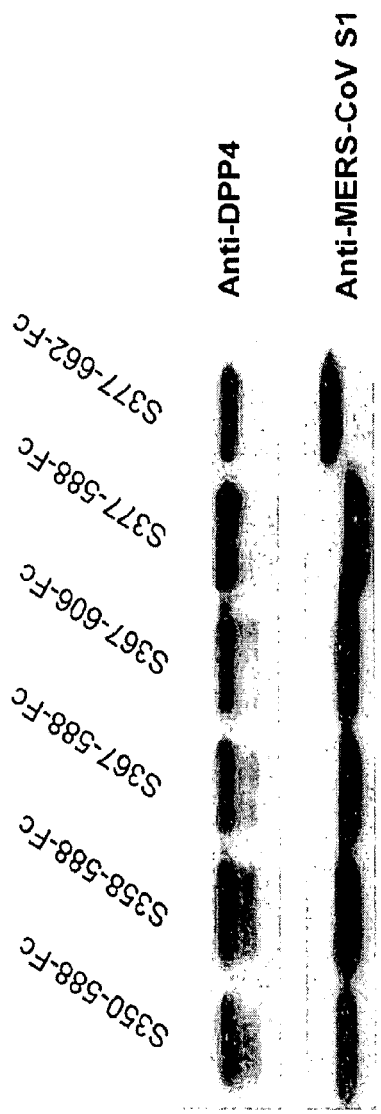
FIG. 12A and FIG. 12B depict the binding of the purified MERS-CoV RBD-Fc proteins to cellular receptor dipeptidyl peptidase 4 (DPP4) in Huh-7 cells by co-immunoprecipitation followed by Western blot (FIG. 12A) and soluble DPP4 (sDPP4) by ELISA (FIG. 12B). Proteins were mixed with Huh-7 cell lysates in the presence of protein A sepharose beads, and detected by Western blot using anti-DPP4 antibodies (1 µg/ml) or antisera from mice immunized with MERS-CoV S1-His (1:1,000), respectively.
Figure 12B:
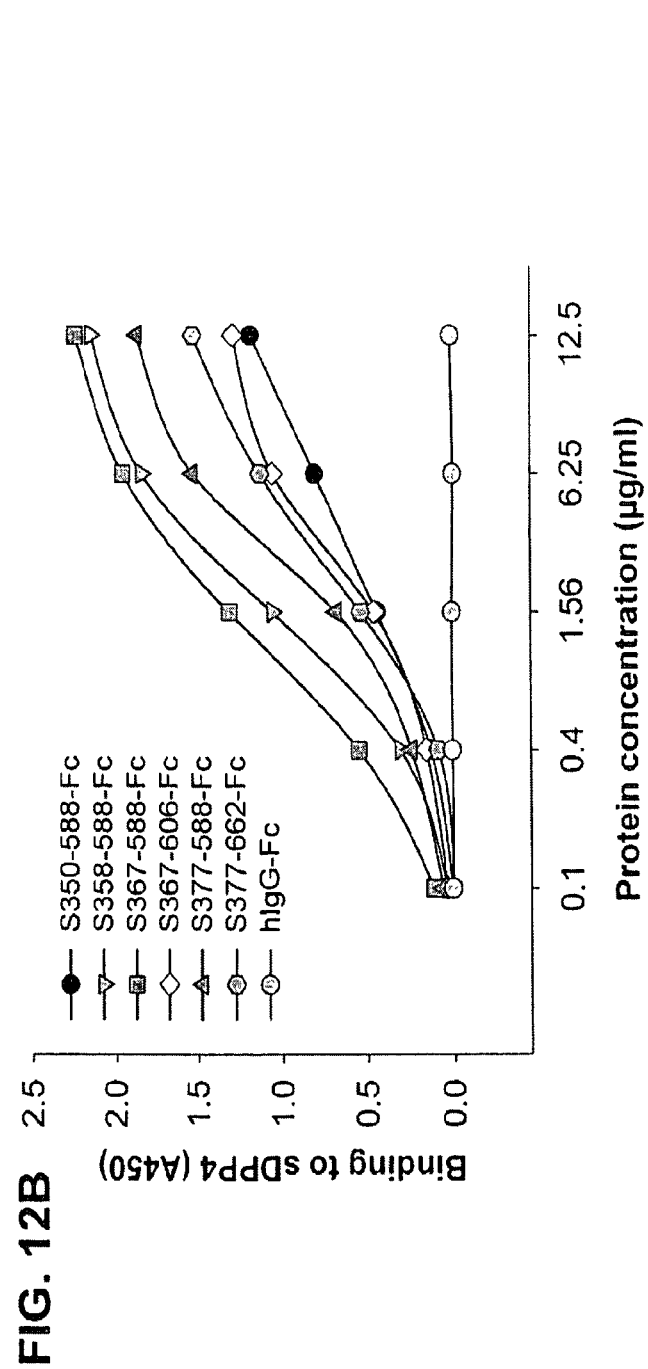
Figure 13B:
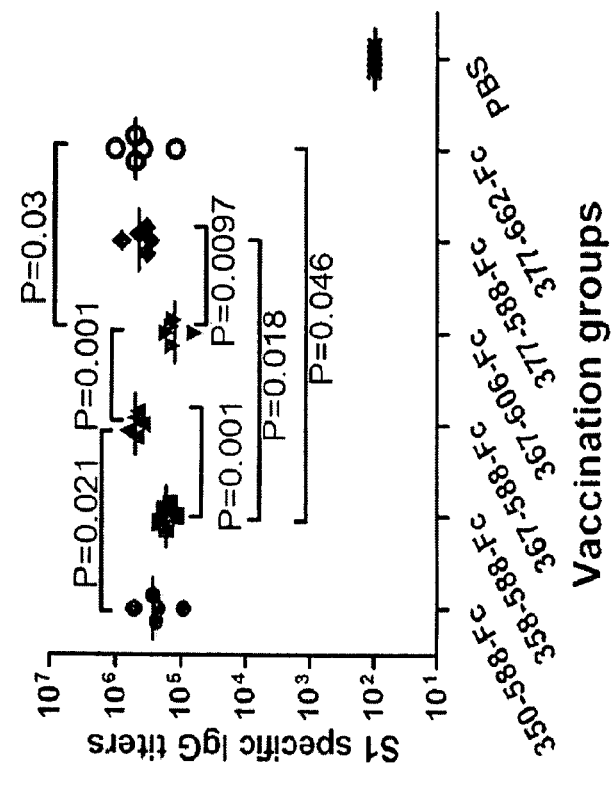
FIG. 13A and FIG. 13B depict IgG antibody responses in sera of mice immunized s.c. with MERS-CoV RBD-Fc proteins. MERS-CoV S1-His protein (S1-His) was used to coat the ELISA plates. Sera from 10 days post-3$^{rd}$ immunization were used for the detection, and the data are presented as mean A450 (FIG. 13A) or mean endpoint titers (FIG. 13B)±SD of five mice per group. Sera of mice injected with PBS were included as the control. P values from different groups were indicated.
Figure 13A:
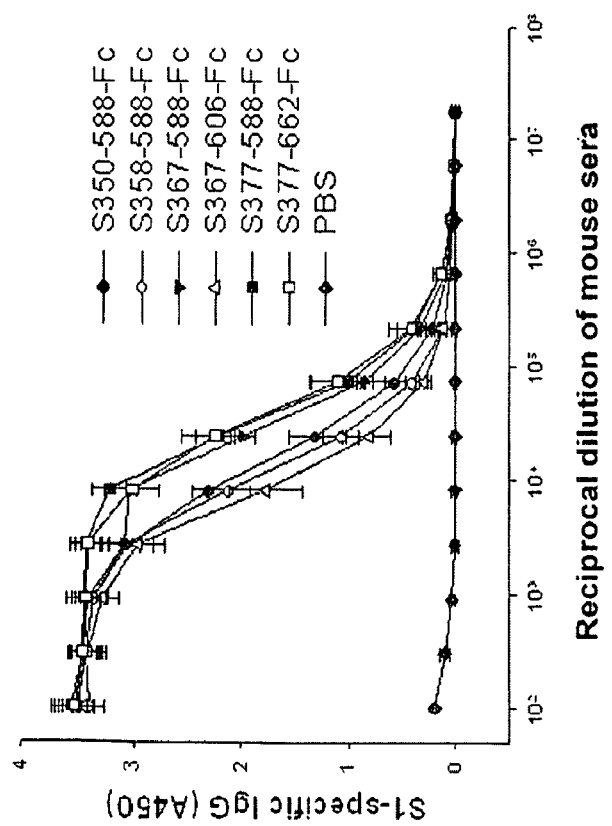
Figure 14:
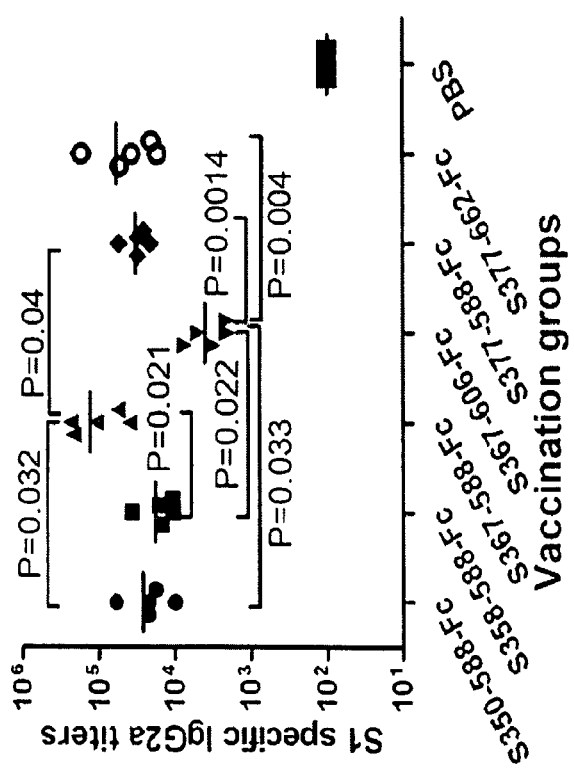
FIG. 14 depicts the IgG subtype antibody responses by ELISA in sera of mice immunized s.c. with MERS-CoV RBD-Fc proteins. MERS-CoV S1-His protein (S1-His) was used to coat the ELISA plates. Sera from 10 days post-3$^{rd}$ immunization were used for the detection, and the data are presented as mean endpoint titers±SD of five mice per group. Sera of mice injected with PBS were included as the control. P values from different groups were indicated.

Structural analysis of MERS-CoV RBD alone or complexed with its receptor DPP4 has identified residues 367-588 or 367-606 of MERS-CoV S1 subunit as the essential RBD (FIG. 10A). To identify the CND in the RBD of MERS-CoV that potentially induces the highest neutralizing antibody response, five additional recombinant proteins were constructed based on the structure-defined RBD of MERS-CoV (FIG. 10B), and these proteins were evaluated for their receptor-binding, antibody responses, and neutralization activity in immunized animals. As shown in FIG. 11A, all five RBD-Fc proteins, namely S350-588-Fc, S358-588-Fc, S367-588-Fc, S377-588-Fc, and S367-606-Fc, were expressed in a mammalian cell expression system at similar expression levels as S377-662-Fc. These proteins are capable of forming suitable conformational structures, having the molecular weight of non-boiled proteins 1-fold higher than that of the boiled proteins, and being recognized by MERS-CoV S1-specific antibodies (FIG. 11B), suggesting the high specificity of these proteins to MERS-CoV. In addition, all proteins bound well to the cellular-associated DPP4 receptor, with two clear bands (corresponding to the size of DPP4 or respective MERS-CoV RBD-Fc monomers) being detected in protein-Huh-7 cell co-immunoprecipitated samples, which reacted strongly with anti-DPP4 and anti-MERS-CoV S1 (FIG. 12A). The ability of these MERS-CoV RBD-Fc proteins in the binding to sDPP4 is notably different, with S367-588-Fc, S358-588-Fc, and S377-588-Fc maintaining higher binding affinity than S377-662-Fc, S367-606-Fc, and S350-588-Fc. As expected, a control protein hIgG-Fc had no binding with sDPP4 (FIG. 12B). The comparison of the humoral immune response in immunized mice indicates that S367-588-Fc, S377-588-Fc, and S377-662-Fc were able to induce higher levels of IgG antibody than S350-588-Fc, S358-588-Fc, and S367-606-Fc (FIGS. 13A and 13B), while S367-588-Fc potentially induced the highest titer of IgG2a subtype specific to the S1 of MERS-CoV (FIG. 14). More importantly, S377-588-Fc elicited the highest neutralizing antibody response among the tested RBD-Fc proteins against MERS-CoV infection (FIG. 15).

The produced MERS pseudovirus was able to efficiently infect a variety of target cells, including DPP4-expressing Huh-7, FRhK-4, MDCK, Vero, Vero E6, HEP-G2, A549, and Caco-2. The infection of MERS pseudovirus in target Huh-7 cells was significantly inhibited by antisera from mice immunized with MERS-CoV RBD-Fc proteins, such as the S377-588-Fc protein.

The S377-588-Fc protein was further characterized and evaluated for the potential as a therapeutic agent against MERS-CoV infection. Antisera from S377-588-Fc immunized mice can effectively block MERS-CoV RBD binding the DPP4 receptor, while control sera from PBS-immunized mice did not show any signs of inhibiting binding of S377-588 to DPP4-expressing Huh-7 cells (FIG. 16). The cross-linker analysis of the conformation of the S377-588-Fc indicates that this protein was able to form dimeric or tetrameric conformational structures (FIG. 17, left), which was confirmed by MERS-CoV S1-specific antibodies (FIG. 17, right). Importantly, the S377-588-Fc protein showed high ability to effectively inhibit MERS-CoV replication in the highly permissive human bronchial epithelial Calu-3 cells that express MERS-CoV's receptor DPP4, with the concentration as low as ~3 μg/ml inhibiting over 50% CPE formation caused by MERS-CoV infection (FIG. 18). These results suggest the use of S377-588-Fc as an important therapeutic agent against infections from MERS-CoV.

In conclusion, disclosed herein are recombinant proteins containing RBD fragments of MERS-CoV S1, a novel critical neutralizing domain of a new human coronavirus, MERS-CoV. These recombinant proteins, based on different fragments of RBD of MERS-CoV S protein linked to human IgG Fc, induced potent neutralizing antibodies against infection by MERS-CoV. Previous studies on S protein-based SARS vaccines have revealed that the mean neutralizing antibody titers as low as 1:284 could protect vaccinated animals against SARS-CoV challenge, suggesting that the expressed recombinant MERS-CoV RBD-Fc proteins have a great potential to be developed as a safe and effective vaccine and therapeutic agent against MERS-CoV infection.

The current study revealed low to no cross-reactivity and cross-neutralizing activity of MERS-CoV with SARS-CoV, suggesting that MERS-CoV has different mechanisms of infection, including using different receptors to infect cells.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A protein comprising:
   a Middle East respiratory syndrome coronavirus (MERS-CoV) spike (S) protein sequence (SEQ ID NO: 1), or fragment thereof wherein said fragment comprises amino acids 350-588 of the MERS-CoV S protein sequence (SEQ ID NO:4), amino acids 358-588 of the MERS-CoV S protein sequence (SEQ ID NO:5), amino acids 367-588 of the MERS-CoV S protein sequence (SEQ ID NO:6), amino acids 377-588 of the MERS-CoV S protein sequence (SEQ ID NO:3), or amino acids 367-606 of the MERS-CoV S protein sequence (SEQ ID NO:7); and
   an immunopotentiator protein sequence, wherein the immunopotentiator sequence comprises an amino acid sequence of an Fc fragment of human IgG (Fc), a C3d protein, an *Onchocerca volvulus* ASP-1, a cholera toxin, a muramyl peptide, or a cytokine.

2. The protein of claim 1, wherein said fragment of the MERS-CoV S protein sequence comprises an MERS-CoV S1 protein sequence, a receptor-binding domain (RBD) sequence of an MERS-CoV S protein, a fusion peptide sequence of an MERS-CoV S protein, a heptad repeat sequence of an MERS-CoV S protein, or a transmembrane domain sequence of an MERS-CoV S protein.

3. The protein of claim 2, the MERS-CoV S1 protein sequence, the RBD sequence of the MERS-CoV S protein, the fusion peptide sequence of the MERS-CoV S protein, the heptad repeat sequence of the MERS-CoV S protein, or the transmembrane domain sequence of the MERS-CoV S protein.

4. The protein of claim 2, the MERS-CoV S1 protein sequence, the RBD sequence of the MERS-CoV S protein, the fusion peptide sequence of the MERS-CoV S protein, the heptad repeat sequence of the MERS-CoV S protein, or the transmembrane domain sequence of the MERS-CoV S protein.

5. The protein of claim 2, wherein the MERS-CoV S1 protein sequence, the RBD sequence of the MERS-CoV S protein, the fusion peptide sequence of the MERS-CoV S protein, the heptad repeat sequence of the MERS-CoV S protein, or the transmembrane domain sequence of the MERS-CoV S protein.

6. The protein of claim 1, wherein the MERS-CoV S protein sequence comprises amino acids 377-588 of the MERS-CoV S protein sequence (SEQ ID NO:3).

7. The protein of claim 1, wherein the immunopotentiator sequence is a human Fc sequence.

8. The protein of claim 1, wherein the protein further comprises a stabilization sequence disposed between the MERS-CoV S protein sequence and the immunopotentiator sequence.

9. The protein of claim 8, wherein the stabilization sequence is a foldon (Fd) or GCN4.

10. The protein of claim 1, wherein the protein further comprises a linker sequence disposed between the MERS-CoV S protein sequence and the immunopotentiator sequence, and the linker is 1 to 8 tandem copies of $(GGGGS)_n$ (SEQ ID NO:24).

11. The protein according to claim 10, wherein n is 1.

12. The protein of claim 1, wherein the protein comprises the sequence of S377-588-Fc (SEQ ID NO:12).

13. An immunogenic composition comprising a protein according to claim 1.

14. A method of inducing a protective immune response against MERS-CoV comprising:
   administering the immunogenic composition of claim 13 to a subject in need thereof;
   wherein the immunogenic composition induces a protective immune response against challenge with MERS-CoV in the host.

15. The method according to claim 14, wherein the immunogenic composition further comprises an adjuvant.

16. The method according to claim 14, wherein the administering step comprises a prime immunization and at least one boost immunization.

17. The method according to claim 16, wherein the boost immunizations are administered at least twice.

18. The method according to claim 17, wherein the boost immunizations are administered weekly, every other week, monthly, or every other month.

19. The method according to claim 17, wherein the boost immunizations are administered weekly, every 2 weeks, every 3 weeks, every 4 weeks, every 5 weeks, every 6 weeks, every 7 weeks, every 8 weeks, every 9 weeks, every 10 weeks, every 11 weeks, or every 12 weeks.

20. The protein of claim 1, wherein said fragment of the MERS-CoV S protein sequence comprises amino acids 350-588 of the MERS-CoV S protein sequence (SEQ ID NO:4).

21. The protein of claim 1, wherein said fragment of the MERS-CoV S protein sequence comprises amino acids 358-588 of the MERS-CoV S protein sequence (SEQ ID NO:5).

22. The protein of claim 1, wherein said fragment of the MERS-CoV S protein sequence comprises amino acids 367-588 of the MERS-CoV S protein sequence (SEQ ID NO:6).

23. The protein of claim 1, wherein said fragment of the MERS-CoV S protein sequence comprises amino acids 367-606 of the MERS-CoV S protein sequence (SEQ ID NO:7).

* * * * *

SEQUENCE LISTING

```
<160> NUMBER OF SEQ ID NOS: 24

<210> SEQ ID NO 1
<211> LENGTH: 1353
<212> TYPE: PRT
<213> ORGANISM: MERS coronavirus

<400> SEQUENCE: 1

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
```

-continued

```
                100                 105                 110
Ala Asn Gly Phe Val Arg Ile Gly Ala Ala Asn Ser Thr Gly
            115                 120                 125
Thr Val Ile Ile Ser Pro Ser Thr Ala Thr Ile Arg Lys Ile Tyr
        130                 135                 140
Pro Ala Phe Met Leu Gly Ser Ser Val Gly Asn Phe Ser Asp Gly Lys
145                 150                 155                 160
Met Gly Arg Phe Phe Asn His Thr Leu Val Leu Leu Pro Asp Gly Cys
                165                 170                 175
Gly Thr Leu Leu Arg Ala Phe Tyr Cys Ile Leu Glu Pro Arg Ser Gly
            180                 185                 190
Asn His Cys Pro Ala Gly Asn Ser Tyr Thr Ser Phe Ala Thr Tyr His
        195                 200                 205
Thr Pro Ala Thr Asp Cys Ser Asp Gly Asn Tyr Asn Arg Asn Ala Ser
210                 215                 220
Leu Asn Ser Phe Lys Glu Tyr Phe Asn Leu Arg Asn Cys Thr Phe Met
225                 230                 235                 240
Tyr Thr Tyr Asn Ile Thr Glu Asp Glu Ile Leu Glu Trp Phe Gly Ile
                245                 250                 255
Thr Gln Thr Ala Gln Gly Val His Leu Phe Ser Ser Arg Tyr Val Asp
            260                 265                 270
Leu Tyr Gly Gly Asn Met Phe Gln Phe Ala Thr Leu Pro Val Tyr Asp
        275                 280                 285
Thr Ile Lys Tyr Tyr Ser Ile Ile Pro His Ser Ile Arg Ser Ile Gln
        290                 295                 300
Ser Asp Arg Lys Ala Trp Ala Ala Phe Tyr Val Tyr Lys Leu Gln Pro
305                 310                 315                 320
Leu Thr Phe Leu Leu Asp Phe Ser Val Asp Gly Tyr Ile Arg Arg Ala
                325                 330                 335
Ile Asp Cys Gly Phe Asn Asp Leu Ser Gln Leu His Cys Ser Tyr Glu
            340                 345                 350
Ser Phe Asp Val Glu Ser Gly Val Tyr Ser Val Ser Ser Phe Glu Ala
        355                 360                 365
Lys Pro Ser Gly Ser Val Val Glu Gln Ala Glu Gly Val Glu Cys Asp
        370                 375                 380
Phe Ser Pro Leu Leu Ser Gly Thr Pro Pro Gln Val Tyr Asn Phe Lys
385                 390                 395                 400
Arg Leu Val Phe Thr Asn Cys Asn Tyr Asn Leu Thr Lys Leu Leu Ser
                405                 410                 415
Leu Phe Ser Val Asn Asp Phe Thr Cys Ser Gln Ile Ser Pro Ala Ala
            420                 425                 430
Ile Ala Ser Asn Cys Tyr Ser Ser Leu Ile Leu Asp Tyr Phe Ser Tyr
        435                 440                 445
Pro Leu Ser Met Lys Ser Asp Leu Ser Val Ser Ser Ala Gly Pro Ile
        450                 455                 460
Ser Gln Phe Asn Tyr Lys Gln Ser Phe Ser Asn Pro Thr Cys Leu Ile
465                 470                 475                 480
Leu Ala Thr Val Pro His Asn Leu Thr Thr Ile Thr Lys Pro Leu Lys
                485                 490                 495
Tyr Ser Tyr Ile Asn Lys Cys Ser Arg Leu Leu Ser Asp Asp Arg Thr
            500                 505                 510
Glu Val Pro Gln Leu Val Asn Ala Asn Gln Tyr Ser Pro Cys Val Ser
        515                 520                 525
```

```
Ile Val Pro Ser Thr Val Trp Glu Asp Gly Asp Tyr Tyr Arg Lys Gln
            530                 535                 540

Leu Ser Pro Leu Glu Gly Gly Trp Leu Val Ala Ser Gly Ser Thr
545                 550                 555                 560

Val Ala Met Thr Glu Gln Leu Gln Met Gly Phe Gly Ile Thr Val Gln
                    565                 570                 575

Tyr Gly Thr Asp Thr Asn Ser Val Cys Pro Lys Leu Glu Phe Ala Asn
                580                 585                 590

Asp Thr Lys Ile Ala Ser Gln Leu Gly Asn Cys Val Glu Tyr Ser Leu
            595                 600                 605

Tyr Gly Val Ser Gly Arg Gly Val Phe Gln Asn Cys Thr Ala Val Gly
    610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
                660                 665                 670

Leu Phe Gly Ser Val Ala Cys Glu His Ile Ser Ser Thr Met Ser Gln
        675                 680                 685

Tyr Ser Arg Ser Thr Arg Ser Met Leu Lys Arg Arg Asp Ser Thr Tyr
    690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
                740                 745                 750

Val Pro Gly Glu Met Arg Leu Ala Ser Ile Ala Phe Asn His Pro Ile
        755                 760                 765

Gln Val Asp Gln Leu Asn Ser Ser Tyr Phe Lys Leu Ser Ile Pro Thr
    770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
                820                 825                 830

Gln Ala Leu His Gly Ala Asn Leu Arg Gln Asp Asp Ser Val Arg Asn
            835                 840                 845

Leu Phe Ala Ser Val Lys Ser Ser Gln Ser Ser Pro Ile Ile Pro Gly
    850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
                900                 905                 910

Met Gln Gln Gly Pro Ala Ser Ala Arg Asp Leu Ile Cys Ala Gln Tyr
            915                 920                 925

Val Ala Gly Tyr Lys Val Leu Pro Pro Leu Met Asp Val Asn Met Glu
    930                 935                 940
```

-continued

```
Ala Ala Tyr Thr Ser Ser Leu Leu Gly Ser Ile Ala Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
            980                 985                 990

Asn Gln Lys Leu Ile Ala Asn Lys Phe Asn Gln Ala Leu Gly Ala Met
        995                 1000                1005

Gln Thr Gly Phe Thr Thr Thr Asn Glu Ala Phe Gln Lys Val Gln
    1010                1015                1020

Asp Ala Val Asn Asn Asn Ala Gln Ala Leu Ser Lys Leu Ala Ser
    1025                1030                1035

Glu Leu Ser Asn Thr Phe Gly Ala Ile Ser Ala Ser Ile Gly Asp
    1040                1045                1050

Ile Ile Gln Arg Leu Asp Val Leu Glu Gln Asp Ala Gln Ile Asp
    1055                1060                1065

Arg Leu Ile Asn Gly Arg Leu Thr Thr Leu Asn Ala Phe Val Ala
    1070                1075                1080

Gln Gln Leu Val Arg Ser Glu Ser Ala Ala Leu Ser Ala Gln Leu
    1085                1090                1095

Ala Lys Asp Lys Val Asn Glu Cys Val Lys Ala Gln Ser Lys Arg
    1100                1105                1110

Ser Gly Phe Cys Gly Gln Gly Thr His Ile Val Ser Phe Val Val
    1115                1120                1125

Asn Ala Pro Asn Gly Leu Tyr Phe Met His Val Gly Tyr Tyr Pro
    1130                1135                1140

Ser Asn His Ile Glu Val Val Ser Ala Tyr Gly Leu Cys Asp Ala
    1145                1150                1155

Ala Asn Pro Thr Asn Cys Ile Ala Pro Val Asn Gly Tyr Phe Ile
    1160                1165                1170

Lys Thr Asn Asn Thr Arg Ile Val Asp Glu Trp Ser Tyr Thr Gly
    1175                1180                1185

Ser Ser Phe Tyr Ala Pro Glu Pro Ile Thr Ser Leu Asn Thr Lys
    1190                1195                1200

Tyr Val Ala Pro Gln Val Thr Tyr Gln Asn Ile Ser Thr Asn Leu
    1205                1210                1215

Pro Pro Pro Leu Leu Gly Asn Ser Thr Gly Ile Asp Phe Gln Asp
    1220                1225                1230

Glu Leu Asp Glu Phe Phe Lys Asn Val Ser Thr Ser Ile Pro Asn
    1235                1240                1245

Phe Gly Ser Leu Thr Gln Ile Asn Thr Thr Leu Leu Asp Leu Thr
    1250                1255                1260

Tyr Glu Met Leu Ser Leu Gln Gln Val Val Lys Ala Leu Asn Glu
    1265                1270                1275

Ser Tyr Ile Asp Leu Lys Glu Leu Gly Asn Tyr Thr Tyr Tyr Asn
    1280                1285                1290

Lys Trp Pro Trp Tyr Ile Trp Leu Gly Phe Ile Ala Gly Leu Val
    1295                1300                1305

Ala Leu Ala Leu Cys Val Phe Phe Ile Leu Cys Cys Thr Gly Cys
    1310                1315                1320

Gly Thr Asn Cys Met Gly Lys Leu Lys Cys Asn Arg Cys Cys Asp
    1325                1330                1335

Arg Tyr Glu Glu Tyr Asp Leu Glu Pro His Lys Val His Val His
```

```
              1340           1345           1350

<210> SEQ ID NO 2
<211> LENGTH: 286
<212> TYPE: PRT
<213> ORGANISM: MERS coronavirus

<400> SEQUENCE: 2

Gln Ala Glu Gly Val Glu Cys Asp Phe Ser Pro Leu Leu Ser Gly Thr
 1               5                  10                  15

Pro Pro Gln Val Tyr Asn Phe Lys Arg Leu Val Phe Thr Asn Cys Asn
             20                  25                  30

Tyr Asn Leu Thr Lys Leu Leu Ser Leu Phe Ser Val Asn Asp Phe Thr
         35                  40                  45

Cys Ser Gln Ile Ser Pro Ala Ala Ile Ala Ser Asn Cys Tyr Ser Ser
     50                  55                  60

Leu Ile Leu Asp Tyr Phe Ser Tyr Pro Leu Ser Met Lys Ser Asp Leu
 65                  70                  75                  80

Ser Val Ser Ser Ala Gly Pro Ile Ser Gln Phe Asn Tyr Lys Gln Ser
                 85                  90                  95

Phe Ser Asn Pro Thr Cys Leu Ile Leu Ala Thr Val Pro His Asn Leu
            100                 105                 110

Thr Thr Ile Thr Lys Pro Leu Lys Tyr Ser Tyr Ile Asn Lys Cys Ser
        115                 120                 125

Arg Leu Leu Ser Asp Asp Arg Thr Glu Val Pro Gln Leu Val Asn Ala
    130                 135                 140

Asn Gln Tyr Ser Pro Cys Val Ser Ile Val Pro Ser Thr Val Trp Glu
145                 150                 155                 160

Asp Gly Asp Tyr Tyr Arg Lys Gln Leu Ser Pro Leu Glu Gly Gly Gly
                165                 170                 175

Trp Leu Val Ala Ser Gly Ser Thr Val Ala Met Thr Glu Gln Leu Gln
            180                 185                 190

Met Gly Phe Gly Ile Thr Val Gln Tyr Gly Thr Asp Thr Asn Ser Val
        195                 200                 205

Cys Pro Lys Leu Glu Phe Ala Asn Asp Thr Lys Ile Ala Ser Gln Leu
    210                 215                 220

Gly Asn Cys Val Glu Tyr Ser Leu Tyr Gly Val Ser Gly Arg Gly Val
225                 230                 235                 240

Phe Gln Asn Cys Thr Ala Val Gly Val Arg Gln Gln Arg Phe Val Tyr
                245                 250                 255

Asp Ala Tyr Gln Asn Leu Val Gly Tyr Tyr Ser Asp Asp Gly Asn Tyr
            260                 265                 270

Tyr Cys Leu Arg Ala Cys Val Ser Val Pro Val Ser Val Ile
        275                 280                 285

<210> SEQ ID NO 3
<211> LENGTH: 212
<212> TYPE: PRT
<213> ORGANISM: MERS coronavirus

<400> SEQUENCE: 3

Gln Ala Glu Gly Val Glu Cys Asp Phe Ser Pro Leu Leu Ser Gly Thr
 1               5                  10                  15

Pro Pro Gln Val Tyr Asn Phe Lys Arg Leu Val Phe Thr Asn Cys Asn
             20                  25                  30

Tyr Asn Leu Thr Lys Leu Leu Ser Leu Phe Ser Val Asn Asp Phe Thr
```

```
            35                  40                  45
Cys Ser Gln Ile Ser Pro Ala Ala Ile Ala Ser Asn Cys Tyr Ser Ser
 50                  55                  60

Leu Ile Leu Asp Tyr Phe Ser Tyr Pro Leu Ser Met Lys Ser Asp Leu
65                  70                  75                  80

Ser Val Ser Ser Ala Gly Pro Ile Ser Gln Phe Asn Tyr Lys Gln Ser
                85                  90                  95

Phe Ser Asn Pro Thr Cys Leu Ile Leu Ala Thr Val Pro His Asn Leu
            100                 105                 110

Thr Thr Ile Thr Lys Pro Leu Lys Tyr Ser Tyr Ile Asn Lys Cys Ser
            115                 120                 125

Arg Leu Leu Ser Asp Asp Arg Thr Glu Val Pro Gln Leu Val Asn Ala
            130                 135                 140

Asn Gln Tyr Ser Pro Cys Val Ser Ile Val Pro Ser Thr Val Trp Glu
145                 150                 155                 160

Asp Gly Asp Tyr Tyr Arg Lys Gln Leu Ser Pro Leu Glu Gly Gly Gly
                165                 170                 175

Trp Leu Val Ala Ser Gly Ser Thr Val Ala Met Thr Glu Gln Leu Gln
            180                 185                 190

Met Gly Phe Gly Ile Thr Val Gln Tyr Gly Thr Asp Thr Asn Ser Val
            195                 200                 205

Cys Pro Lys Leu
    210

<210> SEQ ID NO 4
<211> LENGTH: 239
<212> TYPE: PRT
<213> ORGANISM: MERS coronavirus

<400> SEQUENCE: 4

Ser Tyr Glu Ser Phe Asp Val Glu Ser Gly Val Tyr Ser Val Ser Ser
1               5                   10                  15

Phe Glu Ala Lys Pro Ser Gly Ser Val Val Glu Gln Ala Glu Gly Val
                20                  25                  30

Glu Cys Asp Phe Ser Pro Leu Leu Ser Gly Thr Pro Pro Gln Val Tyr
            35                  40                  45

Asn Phe Lys Arg Leu Val Phe Thr Asn Cys Asn Tyr Asn Leu Thr Lys
 50                  55                  60

Leu Leu Ser Leu Phe Ser Val Asn Asp Phe Thr Cys Ser Gln Ile Ser
65                  70                  75                  80

Pro Ala Ala Ile Ala Ser Asn Cys Tyr Ser Ser Leu Ile Leu Asp Tyr
                85                  90                  95

Phe Ser Tyr Pro Leu Ser Met Lys Ser Asp Leu Ser Val Ser Ser Ala
            100                 105                 110

Gly Pro Ile Ser Gln Phe Asn Tyr Lys Gln Ser Phe Ser Asn Pro Thr
            115                 120                 125

Cys Leu Ile Leu Ala Thr Val Pro His Asn Leu Thr Thr Ile Thr Lys
            130                 135                 140

Pro Leu Lys Tyr Ser Tyr Ile Asn Lys Cys Ser Arg Leu Leu Ser Asp
145                 150                 155                 160

Asp Arg Thr Glu Val Pro Gln Leu Val Asn Ala Asn Gln Tyr Ser Pro
                165                 170                 175

Cys Val Ser Ile Val Pro Ser Thr Val Trp Glu Asp Gly Asp Tyr Tyr
            180                 185                 190
```

```
Arg Lys Gln Leu Ser Pro Leu Glu Gly Gly Trp Leu Val Ala Ser
            195                 200                 205
Gly Ser Thr Val Ala Met Thr Glu Gln Leu Gln Met Gly Phe Gly Ile
    210                 215                 220
Thr Val Gln Tyr Gly Thr Asp Thr Asn Ser Val Cys Pro Lys Leu
225                 230                 235

<210> SEQ ID NO 5
<211> LENGTH: 231
<212> TYPE: PRT
<213> ORGANISM: MERS coronavirus

<400> SEQUENCE: 5

Ser Gly Val Tyr Ser Val Ser Phe Glu Ala Lys Pro Ser Gly Ser
1               5                   10                  15
Val Val Glu Gln Ala Glu Gly Val Glu Cys Asp Phe Ser Pro Leu Leu
            20                  25                  30
Ser Gly Thr Pro Pro Gln Val Tyr Asn Phe Lys Arg Leu Val Phe Thr
        35                  40                  45
Asn Cys Asn Tyr Asn Leu Thr Lys Leu Leu Ser Leu Phe Ser Val Asn
    50                  55                  60
Asp Phe Thr Cys Ser Gln Ile Ser Pro Ala Ala Ile Ala Ser Asn Cys
65                  70                  75                  80
Tyr Ser Ser Leu Ile Leu Asp Tyr Phe Ser Tyr Pro Leu Ser Met Lys
                85                  90                  95
Ser Asp Leu Ser Val Ser Ser Ala Gly Pro Ile Ser Gln Phe Asn Tyr
            100                 105                 110
Lys Gln Ser Phe Ser Asn Pro Thr Cys Leu Ile Leu Ala Thr Val Pro
        115                 120                 125
His Asn Leu Thr Thr Ile Thr Lys Pro Leu Lys Tyr Ser Tyr Ile Asn
    130                 135                 140
Lys Cys Ser Arg Leu Leu Ser Asp Asp Arg Thr Glu Val Pro Gln Leu
145                 150                 155                 160
Val Asn Ala Asn Gln Tyr Ser Pro Cys Val Ser Ile Val Pro Ser Thr
                165                 170                 175
Val Trp Glu Asp Gly Asp Tyr Tyr Arg Lys Gln Leu Ser Pro Leu Glu
            180                 185                 190
Gly Gly Gly Trp Leu Val Ala Ser Gly Ser Thr Val Ala Met Thr Glu
        195                 200                 205
Gln Leu Gln Met Gly Phe Gly Ile Thr Val Gln Tyr Gly Thr Asp Thr
    210                 215                 220
Asn Ser Val Cys Pro Lys Leu
225                 230

<210> SEQ ID NO 6
<211> LENGTH: 222
<212> TYPE: PRT
<213> ORGANISM: MERS coronavirus

<400> SEQUENCE: 6

Glu Ala Lys Pro Ser Gly Ser Val Val Glu Gln Ala Glu Gly Val Glu
1               5                   10                  15
Cys Asp Phe Ser Pro Leu Leu Ser Gly Thr Pro Pro Gln Val Tyr Asn
            20                  25                  30
Phe Lys Arg Leu Val Phe Thr Asn Cys Asn Tyr Asn Leu Thr Lys Leu
        35                  40                  45
```

Leu Ser Leu Phe Ser Val Asn Asp Phe Thr Cys Ser Gln Ile Ser Pro
50                  55                  60

Ala Ala Ile Ala Ser Asn Cys Tyr Ser Ser Leu Ile Leu Asp Tyr Phe
65                  70                  75                  80

Ser Tyr Pro Leu Ser Met Lys Ser Asp Leu Ser Val Ser Ser Ala Gly
                85                  90                  95

Pro Ile Ser Gln Phe Asn Tyr Lys Gln Ser Phe Ser Asn Pro Thr Cys
            100                 105                 110

Leu Ile Leu Ala Thr Val Pro His Asn Leu Thr Thr Ile Thr Lys Pro
        115                 120                 125

Leu Lys Tyr Ser Tyr Ile Asn Lys Cys Ser Arg Leu Leu Ser Asp Asp
130                 135                 140

Arg Thr Glu Val Pro Gln Leu Val Asn Ala Asn Gln Tyr Ser Pro Cys
145                 150                 155                 160

Val Ser Ile Val Pro Ser Thr Val Trp Glu Asp Gly Asp Tyr Tyr Arg
                165                 170                 175

Lys Gln Leu Ser Pro Leu Glu Gly Gly Gly Trp Leu Val Ala Ser Gly
            180                 185                 190

Ser Thr Val Ala Met Thr Glu Gln Leu Gln Met Gly Phe Gly Ile Thr
        195                 200                 205

Val Gln Tyr Gly Thr Asp Thr Asn Ser Val Cys Pro Lys Leu
210                 215                 220

<210> SEQ ID NO 7
<211> LENGTH: 240
<212> TYPE: PRT
<213> ORGANISM: MERS coronavirus

<400> SEQUENCE: 7

Glu Ala Lys Pro Ser Gly Ser Val Val Glu Gln Ala Glu Gly Val Glu
1               5                   10                  15

Cys Asp Phe Ser Pro Leu Leu Ser Gly Thr Pro Pro Gln Val Tyr Asn
                20                  25                  30

Phe Lys Arg Leu Val Phe Thr Asn Cys Asn Tyr Asn Leu Thr Lys Leu
            35                  40                  45

Leu Ser Leu Phe Ser Val Asn Asp Phe Thr Cys Ser Gln Ile Ser Pro
50                  55                  60

Ala Ala Ile Ala Ser Asn Cys Tyr Ser Ser Leu Ile Leu Asp Tyr Phe
65                  70                  75                  80

Ser Tyr Pro Leu Ser Met Lys Ser Asp Leu Ser Val Ser Ser Ala Gly
                85                  90                  95

Pro Ile Ser Gln Phe Asn Tyr Lys Gln Ser Phe Ser Asn Pro Thr Cys
            100                 105                 110

Leu Ile Leu Ala Thr Val Pro His Asn Leu Thr Thr Ile Thr Lys Pro
        115                 120                 125

Leu Lys Tyr Ser Tyr Ile Asn Lys Cys Ser Arg Leu Leu Ser Asp Asp
130                 135                 140

Arg Thr Glu Val Pro Gln Leu Val Asn Ala Asn Gln Tyr Ser Pro Cys
145                 150                 155                 160

Val Ser Ile Val Pro Ser Thr Val Trp Glu Asp Gly Asp Tyr Tyr Arg
                165                 170                 175

Lys Gln Leu Ser Pro Leu Glu Gly Gly Gly Trp Leu Val Ala Ser Gly
            180                 185                 190

Ser Thr Val Ala Met Thr Glu Gln Leu Gln Met Gly Phe Gly Ile Thr
        195                 200                 205

```
Val Gln Tyr Gly Thr Asp Thr Asn Ser Val Cys Pro Lys Leu Glu Phe
    210                 215                 220

Ala Asn Asp Thr Lys Ile Ala Ser Gln Leu Gly Asn Cys Val Glu Tyr
225                 230                 235                 240

<210> SEQ ID NO 8
<211> LENGTH: 468
<212> TYPE: PRT
<213> ORGANISM: artificial sequence
<220> FEATURE:
<223> OTHER INFORMATION: S350-588-Fc peptide

<400> SEQUENCE: 8

Ser Tyr Glu Ser Phe Asp Val Glu Ser Gly Val Tyr Ser Val Ser Ser
1               5                   10                  15

Phe Glu Ala Lys Pro Ser Gly Ser Val Val Gln Ala Glu Gly Val
            20                  25                  30

Glu Cys Asp Phe Ser Pro Leu Leu Ser Gly Thr Pro Pro Gln Val Tyr
        35                  40                  45

Asn Phe Lys Arg Leu Val Phe Thr Asn Cys Asn Tyr Asn Leu Thr Lys
50                  55                  60

Leu Leu Ser Leu Phe Ser Val Asn Asp Phe Thr Cys Ser Gln Ile Ser
65                  70                  75                  80

Pro Ala Ala Ile Ala Ser Asn Cys Tyr Ser Ser Leu Ile Leu Asp Tyr
                85                  90                  95

Phe Ser Tyr Pro Leu Ser Met Lys Ser Asp Leu Ser Val Ser Ser Ala
            100                 105                 110

Gly Pro Ile Ser Gln Phe Asn Tyr Lys Gln Ser Phe Ser Asn Pro Thr
        115                 120                 125

Cys Leu Ile Leu Ala Thr Val Pro His Asn Leu Thr Thr Ile Thr Lys
    130                 135                 140

Pro Leu Lys Tyr Ser Tyr Ile Asn Lys Cys Ser Arg Leu Leu Ser Asp
145                 150                 155                 160

Asp Arg Thr Glu Val Pro Gln Leu Val Asn Ala Asn Gln Tyr Ser Pro
                165                 170                 175

Cys Val Ser Ile Val Pro Ser Thr Val Trp Glu Asp Gly Asp Tyr Tyr
            180                 185                 190

Arg Lys Gln Leu Ser Pro Leu Glu Gly Gly Gly Trp Leu Val Ala Ser
        195                 200                 205

Gly Ser Thr Val Ala Met Thr Glu Gln Leu Gln Met Gly Phe Gly Ile
    210                 215                 220

Thr Val Gln Tyr Gly Thr Asp Thr Asn Ser Val Cys Pro Lys Leu Arg
225                 230                 235                 240

Ser Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335
```

```
Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Glu Glu Met Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
            450                 455                 460

Ser Pro Gly Lys
465

<210> SEQ ID NO 9
<211> LENGTH: 460
<212> TYPE: PRT
<213> ORGANISM: artificial sequence
<220> FEATURE:
<223> OTHER INFORMATION: S358-588-Fc peptide

<400> SEQUENCE: 9

Ser Gly Val Tyr Ser Val Ser Ser Phe Glu Ala Lys Pro Ser Gly Ser
1               5                   10                  15

Val Val Glu Gln Ala Glu Gly Val Glu Cys Asp Phe Ser Pro Leu Leu
            20                  25                  30

Ser Gly Thr Pro Pro Gln Val Tyr Asn Phe Lys Arg Leu Val Phe Thr
            35                  40                  45

Asn Cys Asn Tyr Asn Leu Thr Lys Leu Leu Ser Leu Phe Ser Val Asn
50                  55                  60

Asp Phe Thr Cys Ser Gln Ile Ser Pro Ala Ala Ile Ala Ser Asn Cys
65                  70                  75                  80

Tyr Ser Ser Leu Ile Leu Asp Tyr Phe Ser Tyr Pro Leu Ser Met Lys
            85                  90                  95

Ser Asp Leu Ser Val Ser Ser Ala Gly Pro Ile Ser Gln Phe Asn Tyr
            100                 105                 110

Lys Gln Ser Phe Ser Asn Pro Thr Cys Leu Ile Leu Ala Thr Val Pro
            115                 120                 125

His Asn Leu Thr Thr Ile Thr Lys Pro Leu Lys Tyr Ser Tyr Ile Asn
            130                 135                 140

Lys Cys Ser Arg Leu Leu Ser Asp Asp Arg Thr Glu Val Pro Gln Leu
145                 150                 155                 160

Val Asn Ala Asn Gln Tyr Ser Pro Cys Val Ser Ile Val Pro Ser Thr
            165                 170                 175

Val Trp Glu Asp Gly Asp Tyr Tyr Arg Lys Gln Leu Ser Pro Leu Glu
            180                 185                 190

Gly Gly Gly Trp Leu Val Ala Ser Gly Ser Thr Val Ala Met Thr Glu
            195                 200                 205

Gln Leu Gln Met Gly Phe Gly Ile Thr Val Gln Tyr Gly Thr Asp Thr
            210                 215                 220
```

```
Asn Ser Val Cys Pro Lys Leu Arg Ser Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 10
<211> LENGTH: 451
<212> TYPE: PRT
<213> ORGANISM: artificial sequence
<220> FEATURE:
<223> OTHER INFORMATION: S367-588-Fc peptide

<400> SEQUENCE: 10

Glu Ala Lys Pro Ser Gly Ser Val Val Glu Gln Ala Glu Gly Val Glu
1               5                   10                  15

Cys Asp Phe Ser Pro Leu Leu Ser Gly Thr Pro Pro Gln Val Tyr Asn
                20                  25                  30

Phe Lys Arg Leu Val Phe Thr Asn Cys Asn Tyr Asn Leu Thr Lys Leu
            35                  40                  45

Leu Ser Leu Phe Ser Val Asn Asp Phe Thr Cys Ser Gln Ile Ser Pro
        50                  55                  60

Ala Ala Ile Ala Ser Asn Cys Tyr Ser Ser Leu Ile Leu Asp Tyr Phe
65                  70                  75                  80

Ser Tyr Pro Leu Ser Met Lys Ser Asp Leu Ser Val Ser Ser Ala Gly
                85                  90                  95

Pro Ile Ser Gln Phe Asn Tyr Lys Gln Ser Phe Ser Asn Pro Thr Cys
            100                 105                 110

Leu Ile Leu Ala Thr Val Pro His Asn Leu Thr Thr Ile Thr Lys Pro
        115                 120                 125
```

```
Leu Lys Tyr Ser Tyr Ile Asn Lys Cys Ser Arg Leu Leu Ser Asp Asp
    130                 135                 140

Arg Thr Glu Val Pro Gln Leu Val Asn Ala Asn Gln Tyr Ser Pro Cys
145                 150                 155                 160

Val Ser Ile Val Pro Ser Thr Val Trp Glu Asp Gly Asp Tyr Tyr Arg
                165                 170                 175

Lys Gln Leu Ser Pro Leu Glu Gly Gly Gly Trp Leu Val Ala Ser Gly
            180                 185                 190

Ser Thr Val Ala Met Thr Glu Gln Leu Gln Met Gly Phe Gly Ile Thr
        195                 200                 205

Val Gln Tyr Gly Thr Asp Thr Asn Ser Val Cys Pro Lys Leu Arg Ser
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 11
<211> LENGTH: 469
<212> TYPE: PRT
<213> ORGANISM: artificial sequence
<220> FEATURE:
<223> OTHER INFORMATION: S367-606-Fc peptide

<400> SEQUENCE: 11

Glu Ala Lys Pro Ser Gly Ser Val Val Glu Gln Ala Glu Gly Val Glu
1               5                   10                  15

Cys Asp Phe Ser Pro Leu Leu Ser Gly Thr Pro Pro Gln Val Tyr Asn
                20                  25                  30
```

```
Phe Lys Arg Leu Val Phe Thr Asn Cys Asn Tyr Asn Leu Thr Lys Leu
         35                  40                  45

Leu Ser Leu Phe Ser Val Asn Asp Phe Thr Cys Ser Gln Ile Ser Pro
 50                  55                  60

Ala Ala Ile Ala Ser Asn Cys Tyr Ser Ser Leu Ile Leu Asp Tyr Phe
 65                  70                  75                  80

Ser Tyr Pro Leu Ser Met Lys Ser Asp Leu Ser Val Ser Ser Ala Gly
                 85                  90                  95

Pro Ile Ser Gln Phe Asn Tyr Lys Gln Ser Phe Ser Asn Pro Thr Cys
                100                 105                 110

Leu Ile Leu Ala Thr Val Pro His Asn Leu Thr Thr Ile Thr Lys Pro
             115                 120                 125

Leu Lys Tyr Ser Tyr Ile Asn Lys Cys Ser Arg Leu Leu Ser Asp Asp
         130                 135                 140

Arg Thr Glu Val Pro Gln Leu Val Asn Ala Asn Gln Tyr Ser Pro Cys
145                 150                 155                 160

Val Ser Ile Val Pro Ser Thr Val Trp Glu Asp Gly Asp Tyr Tyr Arg
                165                 170                 175

Lys Gln Leu Ser Pro Leu Glu Gly Gly Gly Trp Leu Val Ala Ser Gly
             180                 185                 190

Ser Thr Val Ala Met Thr Glu Gln Leu Gln Met Gly Phe Gly Ile Thr
         195                 200                 205

Val Gln Tyr Gly Thr Asp Thr Asn Ser Val Cys Pro Lys Leu Glu Phe
    210                 215                 220

Ala Asn Asp Thr Lys Ile Ala Ser Gln Leu Gly Asn Cys Val Glu Tyr
225                 230                 235                 240

Arg Ser Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
             260                 265                 270

Leu Met Ile Ser Arg Thr Pro Glu Val Thr Cys Val Val Val Asp Val
         275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
             340                 345                 350

Pro Ile Glu Lys Thr Ile Ser Lys Ala Lys Gly Gln Pro Arg Glu Pro
         355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
             420                 425                 430

Thr Val Asp Lys Ser Arg Trp Gln Gln Gly Asn Val Phe Ser Cys Ser
         435                 440                 445
```

-continued

Val Met His Glu Ala Leu His Asn His Tyr Thr Gln Lys Ser Leu Ser
     450                 455                 460

Leu Ser Pro Gly Lys
465

<210> SEQ ID NO 12
<211> LENGTH: 441
<212> TYPE: PRT
<213> ORGANISM: artificial sequence
<220> FEATURE:
<223> OTHER INFORMATION: S377-588-Fc peptide

<400> SEQUENCE: 12

Gln Ala Glu Gly Val Glu Cys Asp Phe Ser Pro Leu Leu Ser Gly Thr
1               5                   10                  15

Pro Pro Gln Val Tyr Asn Phe Lys Arg Leu Val Phe Thr Asn Cys Asn
            20                  25                  30

Tyr Asn Leu Thr Lys Leu Leu Ser Leu Phe Ser Val Asn Asp Phe Thr
        35                  40                  45

Cys Ser Gln Ile Ser Pro Ala Ala Ile Ala Ser Asn Cys Tyr Ser Ser
    50                  55                  60

Leu Ile Leu Asp Tyr Phe Ser Tyr Pro Leu Ser Met Lys Ser Asp Leu
65                  70                  75                  80

Ser Val Ser Ser Ala Gly Pro Ile Ser Gln Phe Asn Tyr Lys Gln Ser
                85                  90                  95

Phe Ser Asn Pro Thr Cys Leu Ile Leu Ala Thr Val Pro His Asn Leu
            100                 105                 110

Thr Thr Ile Thr Lys Pro Leu Lys Tyr Ser Tyr Ile Asn Lys Cys Ser
        115                 120                 125

Arg Leu Leu Ser Asp Asp Arg Thr Glu Val Pro Gln Leu Val Asn Ala
130                 135                 140

Asn Gln Tyr Ser Pro Cys Val Ser Ile Val Pro Ser Thr Val Trp Glu
145                 150                 155                 160

Asp Gly Asp Tyr Tyr Arg Lys Gln Leu Ser Pro Leu Glu Gly Gly Gly
                165                 170                 175

Trp Leu Val Ala Ser Gly Ser Thr Val Ala Met Thr Glu Gln Leu Gln
            180                 185                 190

Met Gly Phe Gly Ile Thr Val Gln Tyr Gly Thr Asp Thr Asn Ser Val
        195                 200                 205

Cys Pro Lys Leu Arg Ser Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

```
Pro Arg Glu Pro Gln Val Tyr Thr Leu Pro Pro Ser Arg Glu Glu Met
                340                 345                 350
Thr Lys Asn Gln Val Ser Leu Thr Cys Leu Val Lys Gly Phe Tyr Pro
            355                 360                 365
Ser Asp Ile Ala Val Glu Trp Glu Ser Asn Gly Gln Pro Glu Asn Asn
        370                 375                 380
Tyr Lys Thr Thr Pro Pro Val Leu Asp Ser Asp Gly Ser Phe Phe Leu
385                 390                 395                 400
Tyr Ser Lys Leu Thr Val Asp Lys Ser Arg Trp Gln Gln Gly Asn Val
                405                 410                 415
Phe Ser Cys Ser Val Met His Glu Ala Leu His Asn His Tyr Thr Gln
            420                 425                 430
Lys Ser Leu Ser Leu Ser Pro Gly Lys
        435                 440

<210> SEQ ID NO 13
<211> LENGTH: 515
<212> TYPE: PRT
<213> ORGANISM: artificial sequence
<220> FEATURE:
<223> OTHER INFORMATION: S377-662-Fc peptide

<400> SEQUENCE: 13

Gln Ala Glu Gly Val Glu Cys Asp Phe Ser Pro Leu Leu Ser Gly Thr
1               5                   10                  15
Pro Pro Gln Val Tyr Asn Phe Lys Arg Leu Val Phe Thr Asn Cys Asn
                20                  25                  30
Tyr Asn Leu Thr Lys Leu Leu Ser Leu Phe Ser Val Asn Asp Phe Thr
            35                  40                  45
Cys Ser Gln Ile Ser Pro Ala Ala Ile Ala Ser Asn Cys Tyr Ser Ser
        50                  55                  60
Leu Ile Leu Asp Tyr Phe Ser Tyr Pro Leu Ser Met Lys Ser Asp Leu
65                  70                  75                  80
Ser Val Ser Ser Ala Gly Pro Ile Ser Gln Phe Asn Tyr Lys Gln Ser
                85                  90                  95
Phe Ser Asn Pro Thr Cys Leu Ile Leu Ala Thr Val Pro His Asn Leu
            100                 105                 110
Thr Thr Ile Thr Lys Pro Leu Lys Tyr Ser Tyr Ile Asn Lys Cys Ser
        115                 120                 125
Arg Leu Leu Ser Asp Asp Arg Thr Glu Val Pro Gln Leu Val Asn Ala
130                 135                 140
Asn Gln Tyr Ser Pro Cys Val Ser Ile Val Pro Ser Thr Val Trp Glu
145                 150                 155                 160
Asp Gly Asp Tyr Tyr Arg Lys Gln Leu Ser Pro Leu Glu Gly Gly Gly
                165                 170                 175
Trp Leu Val Ala Ser Gly Ser Thr Val Ala Met Thr Glu Gln Leu Gln
            180                 185                 190
Met Gly Phe Gly Ile Thr Val Gln Tyr Gly Thr Asp Thr Asn Ser Val
        195                 200                 205
Cys Pro Lys Leu Glu Phe Ala Asn Asp Thr Lys Ile Ala Ser Gln Leu
        210                 215                 220
Gly Asn Cys Val Glu Tyr Ser Leu Tyr Gly Val Ser Gly Arg Gly Val
225                 230                 235                 240
Phe Gln Asn Cys Thr Ala Val Gly Val Arg Gln Gln Arg Phe Val Tyr
                245                 250                 255
```

```
Asp Ala Tyr Gln Asn Leu Val Gly Tyr Tyr Ser Asp Asp Gly Asn Tyr
            260                 265                 270

Tyr Cys Leu Arg Ala Cys Val Ser Val Pro Val Ser Val Ile Arg Ser
        275                 280                 285

Asp Lys Thr His Thr Cys Pro Pro Cys Pro Ala Pro Glu Leu Leu Gly
    290                 295                 300

Gly Pro Ser Val Phe Leu Phe Pro Pro Lys Pro Lys Asp Thr Leu Met
305                 310                 315                 320

Ile Ser Arg Thr Pro Glu Val Thr Cys Val Val Val Asp Val Ser His
            325                 330                 335

Glu Asp Pro Glu Val Lys Phe Asn Trp Tyr Val Asp Gly Val Glu Val
        340                 345                 350

His Asn Ala Lys Thr Lys Pro Arg Glu Glu Gln Tyr Asn Ser Thr Tyr
    355                 360                 365

Arg Val Val Ser Val Leu Thr Val Leu His Gln Asp Trp Leu Asn Gly
370                 375                 380

Lys Glu Tyr Lys Cys Lys Val Ser Asn Lys Ala Leu Pro Ala Pro Ile
385                 390                 395                 400

Glu Lys Thr Ile Ser Lys Ala Lys Gly Gln Pro Arg Glu Pro Gln Val
            405                 410                 415

Tyr Thr Leu Pro Pro Ser Arg Glu Glu Met Thr Lys Asn Gln Val Ser
        420                 425                 430

Leu Thr Cys Leu Val Lys Gly Phe Tyr Pro Ser Asp Ile Ala Val Glu
    435                 440                 445

Trp Glu Ser Asn Gly Gln Pro Glu Asn Asn Tyr Lys Thr Thr Pro Pro
450                 455                 460

Val Leu Asp Ser Asp Gly Ser Phe Phe Leu Tyr Ser Lys Leu Thr Val
465                 470                 475                 480

Asp Lys Ser Arg Trp Gln Gln Gly Asn Val Phe Ser Cys Ser Val Met
            485                 490                 495

His Glu Ala Leu His Asn His Tyr Thr Gln Lys Ser Leu Ser Leu Ser
        500                 505                 510

Pro Gly Lys
        515

<210> SEQ ID NO 14
<211> LENGTH: 27
<212> TYPE: PRT
<213> ORGANISM: Bacteriophage T4

<400> SEQUENCE: 14

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 15
<211> LENGTH: 229
<212> TYPE: PRT
<213> ORGANISM: homo sapiens

<400> SEQUENCE: 15

Arg Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30
```

```
Leu Met Ile Ser Arg Thr Pro Glu Val Thr Cys Val Val Asp Val
            35                  40                  45

Ser His Glu Asp Pro Glu Val Lys Phe Asn Trp Tyr Val Asp Gly Val
 50                  55                  60

Glu Val His Asn Ala Lys Thr Lys Pro Arg Glu Glu Gln Tyr Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys
225

<210> SEQ ID NO 16
<211> LENGTH: 234
<212> TYPE: PRT
<213> ORGANISM: mus musculus

<400> SEQUENCE: 16

Arg Ser Pro Arg Gly Pro Thr Ile Lys Pro Cys Pro Pro Cys Lys Cys
1                5                  10                  15

Pro Ala Pro Asn Leu Leu Gly Gly Pro Ser Val Phe Ile Phe Pro Pro
            20                  25                  30

Lys Ile Lys Asp Val Leu Met Ile Ser Leu Ser Pro Ile Val Thr Cys
        35                  40                  45

Val Val Val Asp Val Ser Glu Asp Asp Pro Asp Val Gln Ile Ser Trp
    50                  55                  60

Phe Val Asn Asn Val Glu Val His Thr Ala Gln Thr Gln Thr His Arg
65                  70                  75                  80

Glu Asp Tyr Asn Ser Thr Leu Arg Val Val Ser Ala Leu Pro Ile Gln
                85                  90                  95

His Gln Asp Trp Met Ser Gly Lys Glu Phe Lys Cys Lys Val Asn Asn
            100                 105                 110

Lys Asp Leu Pro Ala Pro Ile Glu Arg Thr Ile Ser Lys Pro Lys Gly
        115                 120                 125

Ser Val Arg Ala Pro Gln Val Tyr Val Leu Pro Pro Pro Glu Glu Glu
    130                 135                 140

Met Thr Lys Lys Gln Val Thr Leu Thr Cys Met Val Thr Asp Phe Met
145                 150                 155                 160

Pro Glu Asp Ile Tyr Val Glu Trp Thr Asn Asn Gly Lys Thr Glu Leu
                165                 170                 175
```

```
Asn Tyr Lys Asn Thr Glu Pro Val Leu Asp Ser Asp Gly Ser Tyr Phe
            180                 185                 190

Met Tyr Ser Lys Leu Arg Val Glu Lys Lys Asn Trp Val Glu Arg Asn
        195                 200                 205

Ser Tyr Ser Cys Ser Val Val His Glu Gly Leu His Asn His His Thr
    210                 215                 220

Thr Lys Ser Phe Ser Arg Thr Pro Gly Lys
225                 230

<210> SEQ ID NO 17
<211> LENGTH: 225
<212> TYPE: PRT
<213> ORGANISM: Oryctolagus cuniculus

<400> SEQUENCE: 17

Arg Ser Ser Lys Pro Thr Cys Pro Pro Pro Glu Leu Leu Gly Gly Pro
1               5                   10                  15

Ser Val Phe Ile Phe Pro Pro Lys Pro Lys Asp Thr Leu Met Ile Ser
            20                  25                  30

Arg Thr Pro Glu Val Thr Cys Val Val Val Asp Val Ser Gln Asp Asp
        35                  40                  45

Pro Glu Val Gln Phe Thr Trp Tyr Ile Asn Asn Glu Gln Val Arg Thr
    50                  55                  60

Ala Arg Pro Pro Leu Arg Glu Gln Gln Phe Asn Ser Thr Ile Arg Val
65                  70                  75                  80

Val Ser Thr Leu Pro Ile Ala His Gln Asp Trp Leu Arg Gly Lys Glu
                85                  90                  95

Phe Lys Cys Lys Val His Asn Lys Ala Leu Pro Ala Pro Ile Glu Lys
            100                 105                 110

Thr Ile Ser Lys Ala Arg Gly Gln Pro Leu Glu Pro Lys Val Tyr Thr
        115                 120                 125

Met Gly Pro Pro Arg Glu Glu Leu Ser Ser Arg Ser Val Ser Leu Thr
    130                 135                 140

Cys Met Ile Asn Gly Phe Tyr Pro Ser Asp Ile Ser Val Glu Trp Glu
145                 150                 155                 160

Lys Asn Gly Lys Ala Glu Asp Asn Tyr Lys Thr Thr Pro Ala Val Leu
                165                 170                 175

Asp Ser Asp Gly Ser Tyr Phe Leu Tyr Ser Lys Leu Ser Val Pro Thr
            180                 185                 190

Ser Glu Trp Gln Arg Gly Asp Val Phe Thr Cys Ser Val Met His Glu
        195                 200                 205

Ala Leu His Asn His Tyr Thr Gln Lys Ser Ile Ser Arg Ser Pro Gly
    210                 215                 220

Lys
225

<210> SEQ ID NO 18
<211> LENGTH: 302
<212> TYPE: PRT
<213> ORGANISM: homo sapiens

<400> SEQUENCE: 18

His Leu Ile Val Thr Pro Ser Gly Cys Gly Glu Gln Asn Met Ile Gly
1               5                   10                  15

Met Thr Pro Thr Val Ile Ala Val His Tyr Leu Asp Glu Thr Glu Gln
            20                  25                  30
```

Trp Glu Lys Phe Gly Leu Glu Lys Arg Gln Gly Ala Leu Glu Leu Ile
              35                  40                  45

Lys Lys Gly Tyr Thr Gln Gln Leu Ala Phe Arg Gln Pro Ser Ser Ala
 50                  55                  60

Phe Ala Ala Phe Val Lys Arg Ala Pro Ser Thr Trp Leu Thr Ala Tyr
 65                  70                  75                  80

Val Val Lys Val Phe Ser Leu Ala Val Asn Leu Ile Ala Ile Asp Ser
                 85                  90                  95

Gln Val Leu Cys Gly Ala Val Lys Trp Leu Ile Leu Glu Lys Gln Lys
                100                 105                 110

Pro Asp Gly Val Phe Gln Glu Asp Ala Pro Val Ile His Gln Glu Met
                115                 120                 125

Ile Gly Gly Leu Arg Asn Asn Asn Glu Lys Asp Met Ala Leu Thr Ala
                130                 135                 140

Phe Val Leu Ile Ser Leu Gln Glu Ala Lys Asp Ile Cys Glu Glu Gln
145                 150                 155                 160

Val Asn Ser Leu Pro Gly Ser Ile Thr Lys Ala Gly Asp Phe Leu Glu
                165                 170                 175

Ala Asn Tyr Met Asn Leu Gln Arg Ser Tyr Thr Val Ala Ile Ala Gly
                180                 185                 190

Tyr Ala Leu Ala Gln Met Gly Arg Leu Lys Gly Pro Leu Leu Asn Lys
                195                 200                 205

Phe Leu Thr Thr Ala Lys Asp Lys Asn Arg Trp Glu Asp Pro Gly Lys
                210                 215                 220

Gln Leu Tyr Asn Val Glu Ala Thr Ser Tyr Ala Leu Leu Ala Leu Leu
225                 230                 235                 240

Gln Leu Lys Asp Phe Asp Phe Val Pro Pro Val Val Arg Trp Leu Asn
                245                 250                 255

Glu Gln Arg Tyr Tyr Gly Gly Tyr Gly Ser Thr Gln Ala Thr Phe
                260                 265                 270

Met Val Phe Gln Ala Leu Ala Gln Tyr Gln Lys Asp Ala Pro Asp His
                275                 280                 285

Gln Glu Leu Asn Leu Asp Val Ser Leu Gln Leu Pro Ser Arg
                290                 295                 300

<210> SEQ ID NO 19
<211> LENGTH: 104
<212> TYPE: PRT
<213> ORGANISM: vibrio cholerae

<400> SEQUENCE: 19

Met Thr Pro Gln Asn Ile Thr Asp Leu Cys Ala Glu Tyr His Asn Thr
1                   5                   10                  15

Gln Ile His Thr Leu Asn Asp Lys Ile Phe Ser Tyr Thr Glu Ser Leu
                20                  25                  30

Ala Gly Lys Arg Glu Met Ala Ile Ile Thr Phe Lys Asn Gly Ala Thr
                35                  40                  45

Phe Gln Val Glu Val Pro Gly Ser Gln His Ile Asp Ser Gln Lys Lys
 50                  55                  60

Ala Ile Glu Arg Met Lys Asp Thr Leu Arg Ile Ala Tyr Leu Thr Glu
 65                  70                  75                  80

Ala Lys Val Glu Lys Leu Cys Val Trp Asn Asn Lys Thr Pro Arg Ala
                 85                  90                  95

Ile Ala Ala Ile Ser Met Ala Asn

-continued

100

<210> SEQ ID NO 20
<211> LENGTH: 29
<212> TYPE: PRT
<213> ORGANISM: Bacteriophage T4

<400> SEQUENCE: 20

Gly Ser Gly Tyr Ile Pro Glu Ala Pro Arg Asp Gly Gln Ala Tyr Val
1               5                   10                  15

Arg Lys Asp Gly Glu Trp Val Leu Leu Ser Thr Phe Leu
            20                  25

<210> SEQ ID NO 21
<211> LENGTH: 32
<212> TYPE: PRT
<213> ORGANISM: Saccharomyces cerevisiae

<400> SEQUENCE: 21

Met Lys Gln Ile Glu Asp Lys Ile Glu Glu Ile Leu Ser Lys Ile Tyr
1               5                   10                  15

His Ile Glu Asn Glu Ile Ala Arg Ile Lys Lys Leu Ile Gly Glu Val
            20                  25                  30

<210> SEQ ID NO 22
<211> LENGTH: 28
<212> TYPE: PRT
<213> ORGANISM: artificial sequence
<220> FEATURE:
<223> OTHER INFORMATION: IQ trimerization sequence

<400> SEQUENCE: 22

Arg Met Lys Gln Ile Glu Asp Lys Ile Glu Glu Ile Glu Ser Lys Gln
1               5                   10                  15

Lys Lys Ile Glu Asn Glu Ile Ala Arg Ile Lys Lys
            20                  25

<210> SEQ ID NO 23
<211> LENGTH: 24
<212> TYPE: PRT
<213> ORGANISM: artificial sequence
<220> FEATURE:
<223> OTHER INFORMATION: IZ trimerization sequence

<400> SEQUENCE: 23

Ile Lys Lys Glu Ile Glu Ala Ile Lys Lys Glu Gln Glu Ala Ile Lys
1               5                   10                  15

Lys Lys Ile Glu Ala Ile Glu Lys
            20

<210> SEQ ID NO 24
<211> LENGTH: 5
<212> TYPE: PRT
<213> ORGANISM: artificial sequence
<220> FEATURE:
<223> OTHER INFORMATION: Linker sequence

<400> SEQUENCE: 24

Gly Gly Gly Gly Ser
1               5